(12) United States Patent
Eversull et al.

(10) Patent No.: US 9,839,771 B2
(45) Date of Patent: *Dec. 12, 2017

(54) EXPANDABLE GUIDE SHEATH AND APPARATUS AND METHODS FOR USING SUCH SHEATHS

(75) Inventors: Christian Scott Eversull, Palo Alto, CA (US); Nicholas J. Mourlas, Mountain View, CA (US); Stephen Arie Leeflang, Sunnyvale, CA (US); Asha Shrinivas Nayak, Menlo Park, CA (US); David John Miller, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 1895 days.

This patent is subject to a terminal disclaimer.

(21) Appl. No.: 12/406,897

(22) Filed: Mar. 18, 2009

(65) Prior Publication Data
US 2009/0182278 A1 Jul. 16, 2009

Related U.S. Application Data

(63) Continuation of application No. 10/423,321, filed on Apr. 24, 2003, now Pat. No. 7,762,995.
(Continued)

(51) Int. Cl.
*A61B 1/00* (2006.01)
*A61M 25/10* (2013.01)
(Continued)

(52) U.S. Cl.
CPC ..... *A61M 25/1027* (2013.01); *A61B 17/3431* (2013.01); *A61B 17/3439* (2013.01);
(Continued)

(58) Field of Classification Search
USPC ............ 604/101, 103, 508, 509, 523, 527; 600/184
See application file for complete search history.

(56) References Cited

U.S. PATENT DOCUMENTS 4,392,853 A 7/1983 Muto
4,401,433 A 8/1983 Luther
(Continued)

FOREIGN PATENT DOCUMENTS

EP 818214 1/1998
WO 8401512 4/1984
(Continued)

OTHER PUBLICATIONS

European Search Report for European Patent Application No. 09156041.7-2319, Applicant: The Board of Trustees of the Leland Stanford Junior University, EPO Forms 1507N, 1503, P0459, 1143 and EPA Form 2906, 9 pages, dated May 8, 2009.

*Primary Examiner* — Elizabeth Houston
*Assistant Examiner* — L. Bachman
(74) *Attorney, Agent, or Firm* — William A. English; Vista IP Law Group LLP

(57) ABSTRACT

Apparatus and methods are provided for accessing body lumens and/or for delivering instruments into body lumens, e.g., vessels within a patient's vasculature. A flexible sheath is provided that is expandable from a contracted condition to an enlarged condition wherein the sheath at least partially defines a lumen therein. The sheath is lubricious and has a relatively thin wall, thereby providing a collapsible/expandable guide for delivering fluids and/or instruments through tortuous anatomy and/or into relatively narrow passages. The sheath is advanced from an entry site to a body lumen in the contracted condition. Once the sheath reaches a target body lumen, the sheath is expanded to the enlarged condition, thereby defining a lumen within the sheath, and fluids
(Continued)

and/or instruments are introduced into the body lumen via the sheath lumen. Upon completing the procedure, the sheath is removed from the body lumen.

27 Claims, 10 Drawing Sheets

Related U.S. Application Data

(60) Provisional application No. 60/376,065, filed on Apr. 25, 2002.

(51) Int. Cl.
*A61B 17/34* (2006.01)
*A61M 25/06* (2006.01)
*A61F 2/95* (2013.01)
*A61F 2/01* (2006.01)
*A61M 25/01* (2006.01)
*A61M 29/02* (2006.01)

(52) U.S. Cl.
CPC .... *A61M 25/0662* (2013.01); *A61M 25/1002* (2013.01); *A61M 25/104* (2013.01); *A61F 2/95* (2013.01); *A61F 2002/011* (2013.01); *A61F 2002/9511* (2013.01); *A61M 25/0668* (2013.01); *A61M 2025/0177* (2013.01); *A61M 2025/0681* (2013.01); *A61M 2025/1004* (2013.01); *A61M 2025/1088* (2013.01); *A61M 2029/025* (2013.01)

(56) References Cited

U.S. PATENT DOCUMENTS

| | | | |
|---|---|---|---|
| 4,406,656 A | 9/1983 | Hattler et al. | |
| 4,451,256 A | 5/1984 | Weikl et al. | |
| 4,569,347 A | 2/1986 | Frisbie | |
| 4,601,713 A | 7/1986 | Fuqua | |
| 4,710,181 A | 12/1987 | Fuqua | |
| 4,738,666 A | 4/1988 | Fuqua | |
| 4,798,193 A | 1/1989 | Hoskins et al. | |
| 4,921,479 A | 5/1990 | Grayzel | |
| 5,015,239 A | 5/1991 | Browne | |
| 5,176,660 A * | 1/1993 | Truckai | 604/527 |
| 5,201,756 A | 4/1993 | Horzewski et al. | |
| 5,209,728 A | 5/1993 | Kraus et al. | |
| 5,234,425 A | 8/1993 | Fogarty et al. | |
| 5,254,084 A | 10/1993 | Geary et al. | |
| 5,256,150 A | 10/1993 | Quiachon et al. | |
| 5,304,134 A | 4/1994 | Kraus | |
| 5,395,349 A | 3/1995 | Quiachon et al. | |
| 5,413,560 A * | 5/1995 | Solar | 604/164.01 |
| 5,431,676 A | 7/1995 | Dubrul et al. | |
| 5,472,418 A | 12/1995 | Palestrant | |
| 5,573,517 A | 11/1996 | Bonutti | |
| 5,618,267 A | 4/1997 | Palestrant | |
| 5,674,240 A | 10/1997 | Bonutti et al. | |
| 5,749,889 A * | 5/1998 | Bacich et al. | 606/198 |
| 5,824,041 A | 10/1998 | Lenker et al. | |
| 5,827,227 A | 10/1998 | DeLago | |
| 5,902,311 A * | 5/1999 | Andreas et al. | 606/144 |
| 5,911,702 A | 6/1999 | Romley et al. | |
| 5,944,691 A | 8/1999 | Querns et al. | |
| 5,961,499 A | 10/1999 | Bonutti et al. | |
| 5,972,441 A | 10/1999 | Campbell et al. | |
| 5,997,508 A | 12/1999 | Lunn et al. | |
| 6,007,517 A | 12/1999 | Anderson | |
| 6,007,522 A | 12/1999 | Agro et al. | |
| 6,090,072 A | 7/2000 | Keith et al. | |
| 6,120,477 A | 9/2000 | Campbell et al. | |
| 6,179,827 B1 * | 1/2001 | Davis et al. | 604/523 |
| 6,183,443 B1 | 2/2001 | Kratoska et al. | |
| 6,197,016 B1 | 3/2001 | Fourkas et al. | |
| 6,338,730 B1 | 1/2002 | Bonutti et al. | |
| 6,361,528 B1 | 3/2002 | Wilson et al. | |
| 6,564,101 B1 * | 5/2003 | Zikria | 607/40 |
| 6,622,731 B2 * | 9/2003 | Daniel et al. | 128/898 |
| 6,652,492 B1 | 11/2003 | Bell et al. | |
| 6,814,715 B2 | 11/2004 | Bonutti et al. | |
| 2001/0053919 A1 | 12/2001 | Kieturakis et al. | |
| 2002/0095117 A1 | 7/2002 | Wilson et al. | |
| 2002/0099431 A1 | 7/2002 | Armstrong et al. | |
| 2002/0165598 A1 | 11/2002 | Wahr et al. | |
| 2003/0065353 A1 | 4/2003 | Horzewski et al. | |
| 2004/0006344 A1 | 1/2004 | Nguyen et al. | |
| 2004/0073286 A1 | 4/2004 | Armstrong et al. | |
| 2004/0087968 A1 | 5/2004 | Core | |

FOREIGN PATENT DOCUMENTS

| | | |
|---|---|---|
| WO | 9729680 | 8/1997 |
| WO | 9829026 | 7/1998 |
| WO | 0032264 | 6/2000 |
| WO | 03090834 | 11/2003 |

* cited by examiner

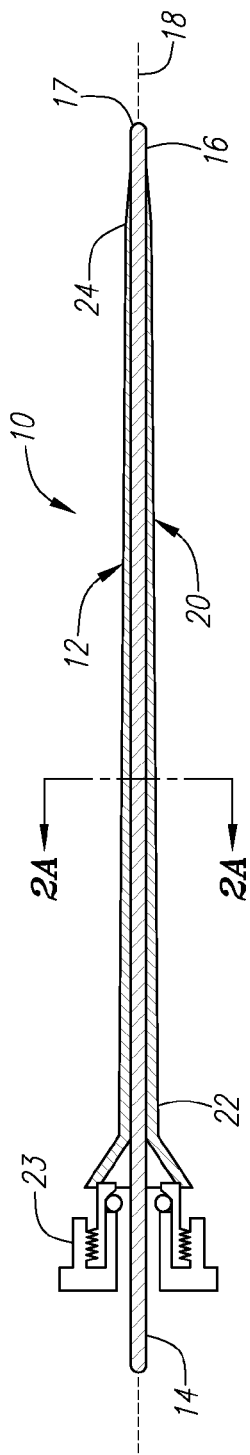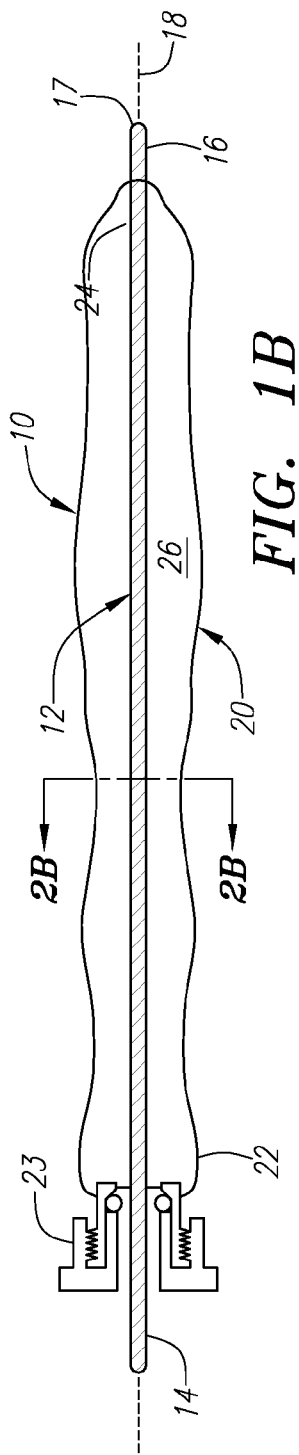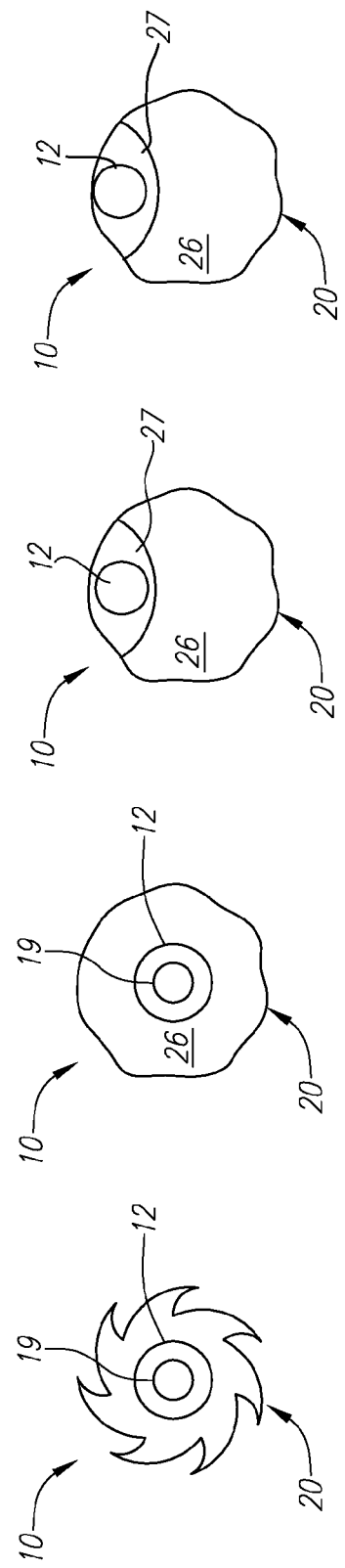

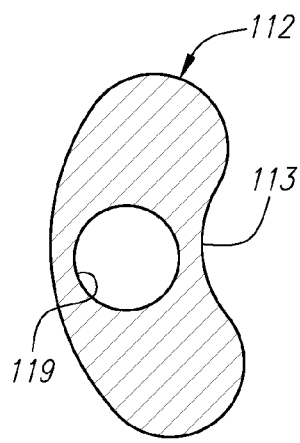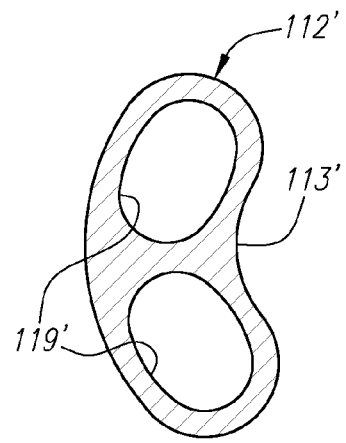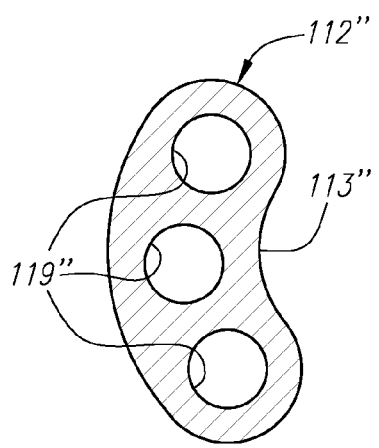
FIG. 3A    FIG. 3B
FIG. 3C
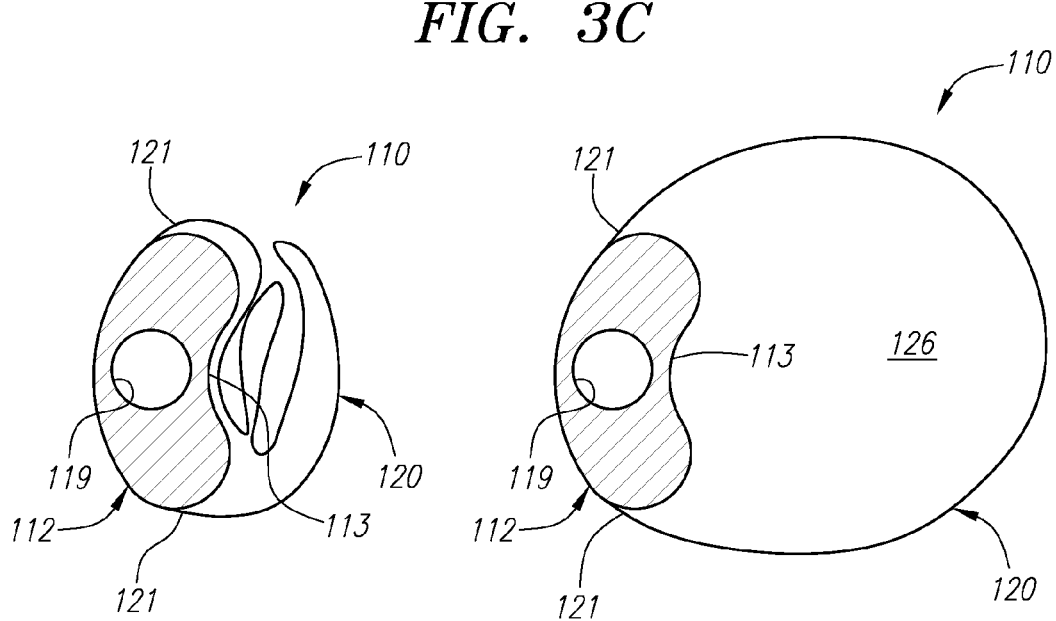
FIG. 4A    FIG. 4B

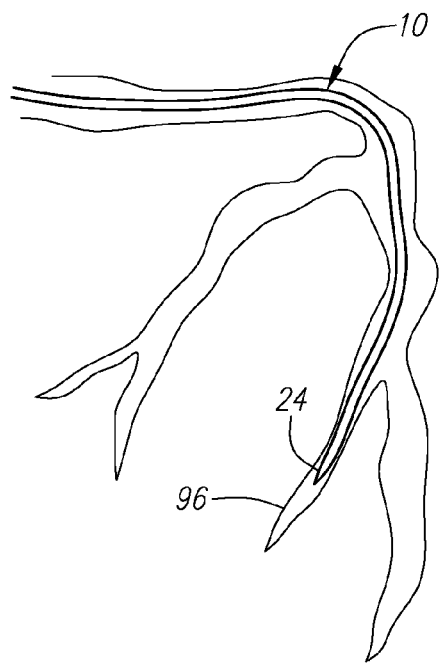
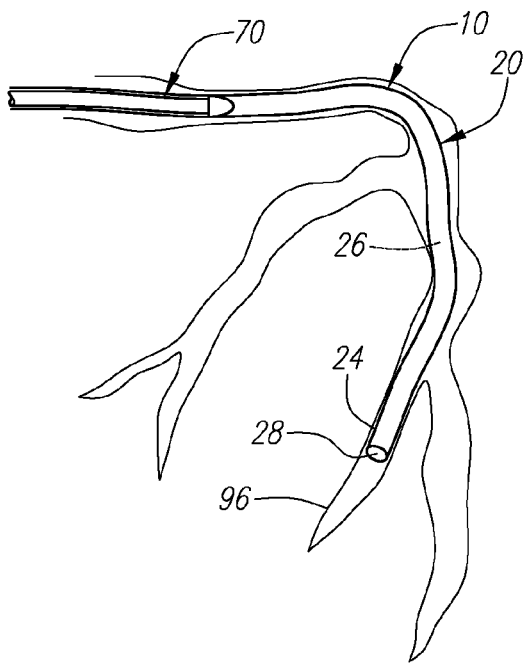
FIG. 12A    FIG. 12B
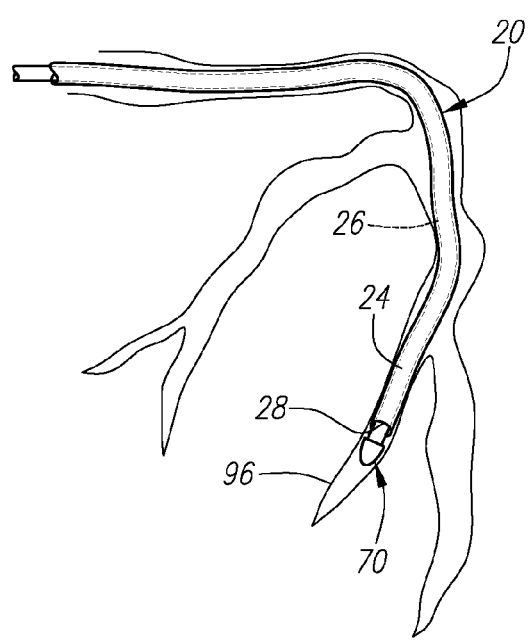
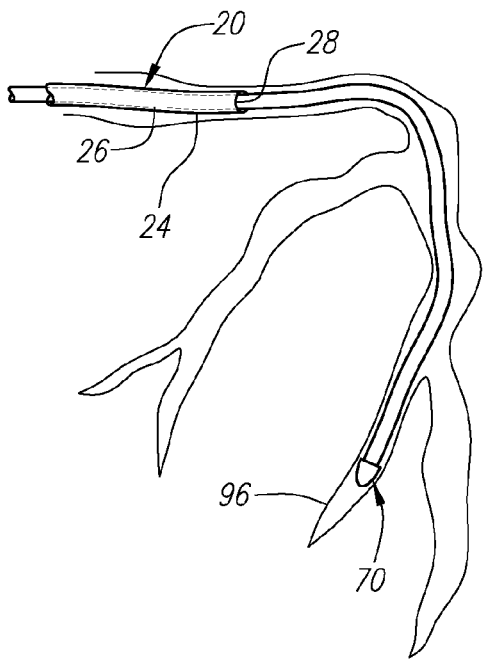
FIG. 12C    FIG. 12D

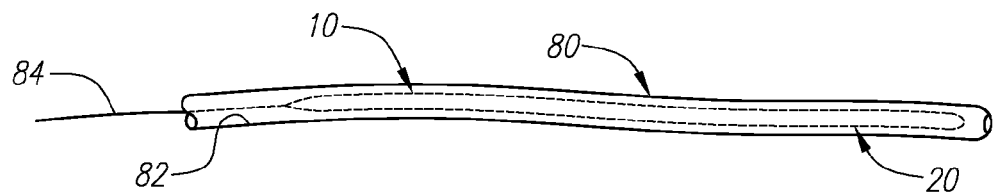
FIG. 13A
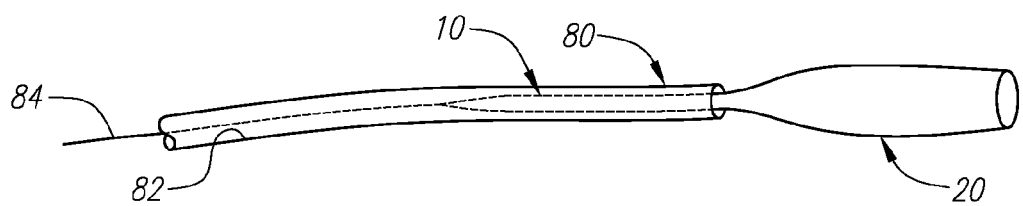
FIG. 13B
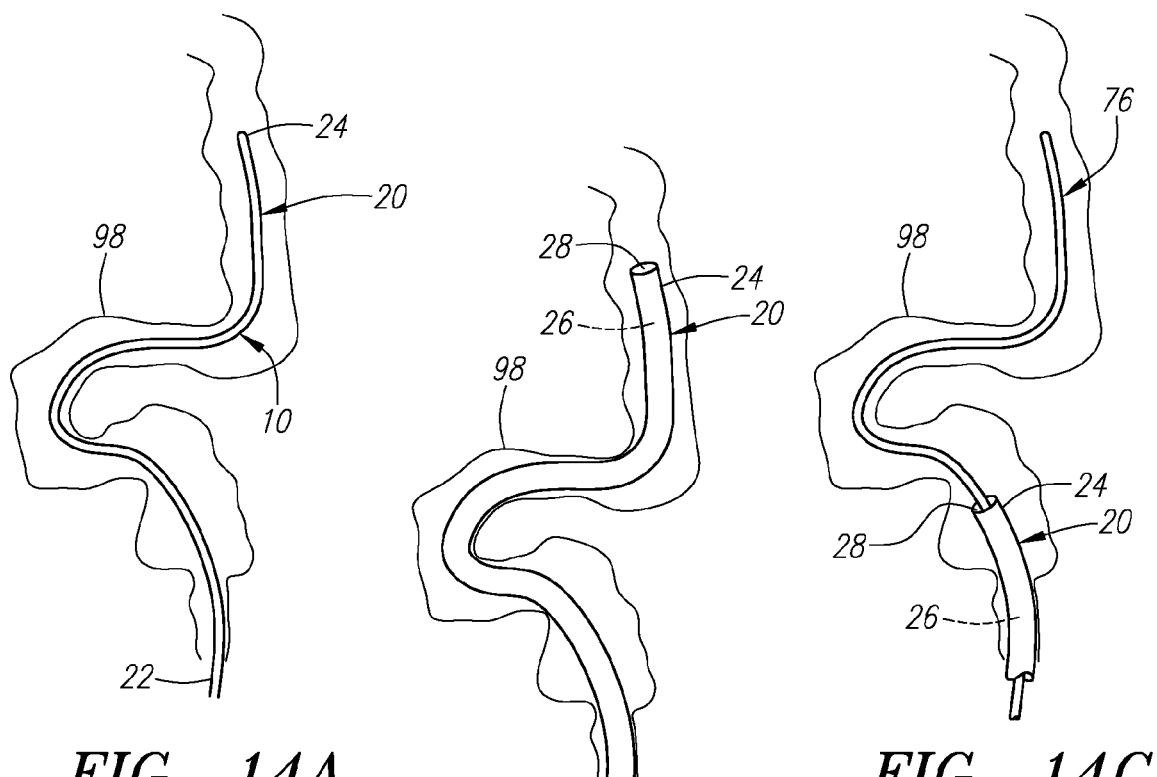
FIG. 14A
FIG. 14B
FIG. 14C

EXPANDABLE GUIDE SHEATH AND APPARATUS AND METHODS FOR USING SUCH SHEATHS

This application is a continuation of co-pending application Ser. No. 10/423,321, filed Apr. 24, 2003, now U.S. Pat. No. 7,762,995, which claims benefit of provisional application Ser. No. 60/376,065, filed Apr. 25, 2002, the disclosure of which is expressly incorporated herein by reference.

FIELD OF THE INVENTION

The present invention relates generally to apparatus and methods for delivering instruments and/or agents during a medical procedure, and, more particularly, to guide sheaths for accessing body lumens and/or delivering instruments into body lumens of a patient.

BACKGROUND

Minimally invasive procedures have been implemented in a variety of medical settings, e.g., for vascular interventions, such as angioplasty, stenting, embolic protection, electrical heart stimulation, heart mapping and visualization, and the like. These procedures generally rely on accurately navigating and placing instruments within a patient's vasculature.

During such procedures, a target vessel may be accessed using a guidewire advanced through the intervening vasculature into the target vessel, thereby providing a "railway" to the vessel. One or more instruments, e.g., catheters, sheaths, and the like, may be advanced over the guidewire or "rail" into the vessel. Thus, a diagnostic and/or therapeutic procedure may be performed by advancing one or more instruments over this railway.

There are many risks involved with advancing instruments over a guidewire. For example, a catheter or other instrument may skive or otherwise damage a wall of a vessel, particularly as the instrument passes through narrow passages or tortuous anatomy involving sharp bends. Such instruments also risk dislodging embolic material or even perforating the vessel wall.

In addition, it is often desirable to access very small vessels deep within the body, e.g., within a patient's heart, for example, to place a ventricular pacing lead within a coronary vein. However, the instrument(s), e.g., guide sheath, lead, etc., may have a relatively large cross-section and/or may have a relatively blunt distal tip, making it difficult to advance such instruments as deeply as desired into such small vessels.

Accordingly, apparatus and methods for delivering instruments into blood vessels or other body lumens and/or for otherwise accessing vessels or other body lumens would be useful.

SUMMARY OF THE INVENTION

The present invention is directed generally to apparatus and methods for providing access to body lumens and/or for delivering instruments and/or agents into body lumens during a medical procedure. More particularly, the present invention is directed to guide sheaths and methods for using such sheaths to facilitate delivering instruments and/or agents into body lumens of a patient, e.g., within the patient's coronary, neuro, and/or peripheral vasculature, within the patient's gastrointestinal tract, urogenital tract, respiratory tract, lymphatic system, and/or within surgically created passages.

In accordance with one aspect of the present invention, a sheath apparatus is provided that includes an elongate expandable sheath that may be expandable from a contracted condition to minimize a profile of the sheath, e.g., to allow insertion into a body lumen, to an enlarged condition wherein the sheath at least partially defines a lumen therein. The sheath may be formed from a lubricious material, a polymer, and/or an elastomeric material, preferably having a relatively thin wall, thereby providing a tubular sheath that may be substantially flexible and/or flimsy. For example, the sheath may include a wall thickness between about 0.001-1.25 millimeter, and preferably between about 0.005-0.06 millimeter.

Optionally, the sheath may include one or more reinforcing elements extending along the sheath, e.g., axially, helically, and/or circumferentially around the sheath. Such reinforcing elements may support the sheath during delivery and/or may enhance the sheath assuming a desired shape and/or size in the enlarged condition. In addition or alternatively, a stiffening or reinforcing member may be provided for supporting or otherwise carrying the sheath to facilitate its introduction in the contracted condition. Optionally, the sheath and/or stiffening member(s) may be coated, e.g., with an anti-thrombotic agent and/or hydrophilic coating.

Preferably, the expandable sheath includes a proximal end, a distal end, and has a length sufficient to extend between an entry site into a patient's body and a target body lumen, e.g., between about two and three hundred centimeters (2-300 cm), and preferably between about twenty and one hundred fifty centimeters (20-150 cm). In one embodiment, the sheath may be a tubular member, while, in another embodiment, the sheath may include a sheet of material whose edges are attached to a stiffening member such that the sheet and the stiffening member together define the lumen.

The distal end of the sheath may include an opening communicating with the lumen such that an instrument inserted through the lumen may be advanced from the opening into a body lumen. Alternatively, the distal end of the sheath may be substantially closed and/or may include a break-away portion for creating an opening such that an instrument inserted through the lumen may be advanced from the opening into a body lumen. Optionally, the sheath may include a fixation device, e.g., an expandable cuff or balloon, on the distal end for substantially securing the apparatus at a location within a body lumen, e.g., to prevent movement during delivery of a treatment device through the sheath.

In accordance with another aspect of the present invention, an apparatus is provided that includes a flexible stiffening member having proximal and distal ends, and an expandable sheath. The sheath may extend between the proximal and distal ends of the stiffening member, and may be expandable from a contracted condition to minimize a profile of the sheath, and an enlarged condition wherein the sheath at least partially defines a lumen extending at least partially between the proximal and distal ends of the stiffening member. Similar to the previous embodiments, the sheath may be formed from a lubricious material, a polymer, and/or an elastomeric material, preferably having a relatively thin, flexible and/or flimsy wall.

The stiffening member may include one or more strands extending along the sheath, e.g., extending axially, helically, and/or circumferentially around the sheath. In a preferred embodiment, the stiffening member is an elongate member for carrying the sheath and having sufficient column strength that the distal end of the stiffening member may be advanced through a body lumen by pushing the proximal end of the stiffening member without substantial risk of kinking or buckling. For example, the stiffening member may be a guidewire, a catheter, or other cylindrical member about which the sheath may be wrapped or otherwise maintained in the contracted condition. Alternatively, the stiffening member may include an arcuate cross-section, thereby defining a groove extending between the proximal and distal ends within which the sheath may be at least partially disposed in the contracted condition.

The sheath may be attached to the stiffening member at one or more locations, e.g., at the distal end of the stiffening member, at both the proximal and distal ends of the stiffening member, at intermediate locations between the proximal and distal ends, and/or continuously along the stiffening member. In addition or alternatively, the sheath may be detachably secured to the stiffening member. Optionally, a constraint may be provided for selectively maintaining the sheath in the contracted condition. For example, the stiffening member and sheath may be disposed within a catheter or other tubular member, and/or one or more filaments may be disposed around the sheath to maintain the sheath in the contracted condition.

In accordance with yet another aspect of the present invention, a method is provided for accessing a body lumen of a patient. The body lumen may be, for example, a vessel or other passage within a patient's urogenital tract, respiratory tract, gastrointestinal tract, lymphatic system, or vascular system. In addition or alternatively, the body lumen may be a passage surgically created within the patient, e.g., an interstitial space accessed via a surgically-created entry site.

Generally, an expandable sheath is advanced from an entry site to a body lumen with the sheath in a contracted condition. The sheath may be advanced over a guide wire or in conjunction with another rail. Preferably, the sheath is advanced from the entry site until a distal end of the sheath is disposed within the body lumen while a proximal end of the sheath remains outside the entry site.

Once the sheath reaches the target body lumen, the sheath may be expanded to an enlarged condition, thereby defining a lumen within the sheath, e.g., that extends from the entry site to the target body lumen. The sheath may be expanded to the enlarged condition, e.g., by introducing a fluid into the lumen defined by the sheath, such as saline, contrast, carbon dioxide, oxygen, and/or air, and/or by introducing an instrument into the lumen defined by the sheath.

A diagnostic and/or therapeutic procedure may be performed within the body lumen via the lumen defined by the sheath. In one embodiment, the entry site may be a percutaneous site communicating with the patient's vasculature, and the body lumen may be a blood vessel, e.g., within the patient's coronary, peripheral, or neuro vasculature. The procedure may include introducing one or more instruments or agents through the lumen defined by the sheath into the target blood vessel, e.g., a catheter, a guidewire, a balloon, a stent, a filter, a pacing lead, an atherectomy device, a thrombectomy device, and/or a medicament (e.g., anti-inflammatory drug, anti-thrombotic agent, inhibitors, and the like). In a preferred embodiment, the target blood vessel may be a stenotic or occluded region within an artery. In another preferred embodiment, the target blood vessel may be a coronary vein, and the one or more instruments may include an electrical lead.

Upon completing the procedure, the sheath may be removed from the body lumen. Optionally, the sheath may be at least partially collapsed from the enlarged condition before removing the sheath from the body lumen, e.g., by creating a vacuum within the sheath and/or by withdrawing the sheath into a catheter or other tubular member. Alternatively, the sheath may be split along a single longitudinal seam, or along two or more seams into two or more pieces to facilitate removal from the body lumen.

Thus, a sheath in accordance with the present invention may provide a primary access device that is substantially flexible, collapsible, and/or compliant. This primary device may assume a relatively low profile to facilitate advancement through narrow passages and/or tortuous anatomy, e.g., into difficult to access locations deep within a patient's body. Once a desired location is reached, the primary device may be released and/or expanded, and one or more secondary device(s) may be advanced through the primary device. The primary device may provide a lubricious path, prevent dissection of a vessel wall, and/or otherwise facilitate delivering the secondary device(s) into difficult to access locations. The primary device may be free to expand to accommodate the secondary device(s) and/or to substantially translate axial forces, e.g., caused by pushing the secondary device(s), into radial forces, thereby minimizing risk of damage to the passages through which the secondary device(s) is(are) advanced.

In accordance with another aspect of the present invention, an apparatus is provided for delivering an instrument, e.g., a guidewire, into a body lumen of a patient, e.g., across a total occlusion within a blood vessel. The apparatus generally includes a catheter or other elongate and/or tubular member including proximal and distal ends, and an expandable sheath attached to an outer surface of the catheter. The sheath, e.g., a flexible and/or flimsy tubular member and/or sheet, may be expandable from a contracted condition to minimize a profile of the sheath, and an enlarged condition wherein the sheath at least partially defines an accessory lumen extending between proximal and distal ends of the sheath.

In accordance with yet another aspect of the present invention, a method is provided for delivering an instrument through an occlusion in a body lumen using a catheter or other elongate member including an expandable sheath extending along an outer surface of the elongate member. A distal end of the catheter may be introduced into the body lumen proximal to the occlusion with the sheath in a contracted condition. The distal end of the catheter may be advanced through the occlusion until a distal end of the sheath is disposed distal to the occlusion. The distal end of the catheter may include one or more elements for facilitating advancing the distal end through the occlusion, e.g., an imaging element, a dissection element, and/or a steering element.

An instrument, e.g., a guidewire or other elongate member, may be advanced through the sheath until a distal end of the instrument is disposed distal to the occlusion. The sheath may be expanded before inserting the instrument, e.g., by introducing fluid into the lumen of the sheath, or the sheath may be expanded as the instrument is inserted into the sheath.

The catheter and sheath may then be withdrawn from the body lumen, e.g., leaving the guidewire or other elongate member across the occlusion. One or more instruments may be advanced over the guidewire, e.g., after the catheter is withdrawn to observe and/or treat the occlusion.

Other objects and features of the present invention will become apparent from consideration of the following description taken in conjunction with the accompanying drawings.

BRIEF DESCRIPTION OF THE DRAWINGS

FIGS. 1A and 1B are partial cross-sectional side views of a first preferred embodiment of a sheath apparatus, including an expandable sheath and a stiffening member, showing the sheath in contracted and expanded conditions, respectively.

FIGS. 2A and 2B are cross-sections of the apparatus of FIGS. 1A and 1B taken along lines 2A and 2B, respectively.

FIGS. 3A-3C are alternate cross-sections of a stiffening member that may be incorporated into a sheath apparatus.

FIGS. 4A and 4B are cross-sectional views of an alternative embodiment of a sheath apparatus, including an expandable sheath attached to a stiffening member, such as that shown in FIG. 3A, showing the sheath in contracted and expanded conditions, respectively.

FIGS. 12A-12D are partial cross-sections of a patient's heart, showing a method for delivering an electrical lead into a coronary vein using a sheath apparatus, in accordance with the present invention.

FIGS. 13A and 13B are side views of another embodiment of a sheath apparatus including a tubular constraint from which the apparatus may be deployed.

FIGS. 14A-14C are partial cross-sectional views of a patient's colon, showing a method for delivering a colonoscope using a sheath apparatus, in accordance with the present invention.

FIGS. 21A and 21B are cross-sections of alternate embodiments of the apparatus of FIGS. 1A and 1B.

DETAILED DESCRIPTION OF THE PREFERRED EMBODIMENTS

Figure 5:
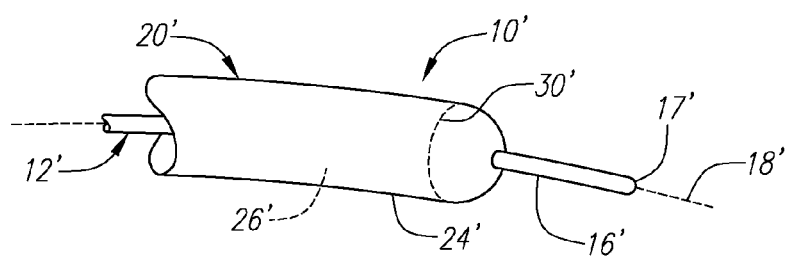
FIG. 5 is a perspective detail of a distal end of a sheath apparatus, including an expandable sheath having a weakened region for creating an opening in a wall thereof

Turning to the drawings, FIGS. 1A-2B show a first preferred embodiment of an apparatus 10 for providing access within a body lumen (not shown) and/or for delivering one or more instruments (also not shown) within a body lumen, such as a vessel within a patient's vasculature, a passage within a patient's gastrointestinal tract, urogenital tract, respiratory tract, lymphatic system, and the like.

Generally, the apparatus 10 includes a flexible elongate stiffening member 12 providing a "backbone" for the apparatus 10, and an expandable membrane or sheath 20. The stiffening member 12 includes a proximal end 14 and a distal end 16 defining a longitudinal axis 18 therebetween. In addition, the stiffening member 12 may have sufficient length to be advanced from a location outside a patient's body (not shown) through any intervening body passages into a site to be accessed and/or treated. The distal end 16 may have a size and/or shape for insertion into a body lumen, e.g., including a rounded or other substantially atraumatic distal tip 17, a "J" tip (not shown), and the like.

In one embodiment, the stiffening member 12 may be a solid or hollow guidewire, a catheter, a thread, and the like. Preferably, the stiffening member 12 is substantially flexible to facilitate advancement through tortuous anatomy without causing dissection or perforation, yet has sufficient column strength and/or torque-ability that the distal end 16 may be advanced through a body lumen by pushing the proximal end 14 without substantial risk of kinking and/or buckling. The stiffening member 12 may include one or more lumens 19 (shown in FIGS. 2A and 2B) extending between the proximal and distal ends 14, 16, e.g., to allow fluids to be delivered therethrough and/or to receive a guide wire or other instrument (not shown) therethrough.

The stiffening member 12 may have a substantially symmetrical cross-section, e.g., a cylindrical cross-section, as shown in FIGS. 2A and 2B, or may have an asymmetrical cross-section, e.g., an arcuate cross-section, as shown in FIGS. 3A-4B. In the embodiments shown in FIGS. 3A-4B, the stiffening member 112 may define a groove 113 extending at least partially between its proximal and distal ends (not shown in FIGS. 3A-4B).

The stiffening member 12 or 112 may be formed from a variety of materials and using various methods known in the art. For example, the stiffening member may be formed from plastic, glass, composite, and/or metal using known methods, such as extrusion and the like, thereby providing a desired combination of flexibility and column strength. As used herein, the terms "backbone," "backbone member," or "stiffening member" may include any elongate flexible structure capable of supporting or reinforcing an expandable membrane or other sheath to facilitate introducing the sheath into a body lumen of a patient and/or to facilitate tracking a secondary device along the axis of the sheath and/or over the entire apparatus. The stiffening member 12 may have a diameter or other maximum cross-section between about 0.05-5 millimeters, and preferably between about 0.2-2 millimeters.

Returning to FIGS. 1A and 1B, the expandable membrane or sheath 20 includes a proximal end 22, a distal end 24, and one or more side walls extending between the proximal and distal ends 22, 24, thereby at least partially defining a lumen 26. As used herein, the term "sheath" or "guide sheath" may include any structure that at least partially defines a lumen, whether the structure is substantially tubular or only partially defines the lumen.

The sheath 20 may be expandable from a contracted condition, as shown in FIGS. 1A and 2A, to an enlarged condition, as shown in FIGS. 1B and 2B. When the sheath 20 is in a contracted condition, the apparatus 10 may assume a low profile to facilitate insertion into a body lumen (not shown). For example, as best seen in FIG. 2A, the sheath 20 may be folded, twisted, wrapped, or otherwise compressed around or adjacent to the stiffening member 12 (e.g., using an internal vacuum with the lumen 26 of the sheath 20 and/or an external force). In the enlarged condition, the sheath 20 may unfold, untwist, unwrap, or otherwise expand to at least partially define the lumen 26, e.g., for receiving a fluid (e.g., a medicament, anti-thrombotic agent, and the like) and/or one or more instruments therethrough (not shown).

Because the sheath 20 is relatively thin-walled, the apparatus 10 may attain a relatively low profile when the sheath 20 is in its contracted condition, e.g., between about 0.1 and about ten millimeters (0.1-10 mm), and preferably between about 0.2 and about three millimeters (0.2-3 mm). Conversely, a relatively large lumen 26 may be provided when the sheath 20 is expanded to the enlarged condition, e.g., having a diameter or other maximum cross-section between about 0.3 and about one hundred millimeters (0.3-100 mm), and preferably between about 0.3 and about twenty millimeters (0.3-20 mm).

The sheath 20 may be formed from relatively thin, flexible material, as compared to the stiffening member 12. Thus, the sheath 20 may be flimsy, i.e., may have little or no rigidity such that the sheath 20 provides little resistance to expansion and/or contraction, and/or may conform substantially to anatomy within which it is deployed. As used herein, "flimsy" means that the material of the sheath 20 is not biased to assume any particular configuration or shape, and therefore, the sheath 20 may adopt whatever shape and/or configuration that is imposed upon it, e.g., by being folded or otherwise compressed, by being subjected to internal pressure or force, and the like. To achieve this, the sheath 20 may have a relatively thin wall thickness, e.g., between about 0.001-1.25 millimeters, and preferably between about 0.005-0.06 millimeter.

The sheath 20 may be constructed of materials that may be fabricated to a relatively thin, flexible configuration, e.g., polytetrafluoroethylene (PTFE), expanded polytetrafluoroethylene (EPTFE), fluorinated ethylene propylene (FEP), polyethylene teraphathalate (PET), urethane, olefins, polyethylene (PE), silicone, latex, isoprene, chronoprene; and the like. The sheath 20 may be formed from a lubricious material and/or hydrophilically coated with a liquid silicone or other coating, e.g., for facilitating inserting one or more instruments (not shown) through the lumen 26. Preferably, the sheath 20 is formed from substantially inelastic material, i.e., such that a primary contribution to the sheath 20 expanding and contracting is unfolding or folding the material of the sheath 20. Thus, a total peripheral length of the sheath 20 may not change substantially between the contracted and enlarged conditions. Alternatively, the sheath 20 may be formed from an elastic material such that a secondary contribution to the sheath 20 expanding and contracting is an elasticity of the material of the sheath 20, i.e., such that the peripheral length of the sheath 20 may increase as the sheath 20 expands towards the enlarged condition.

The sheath 20 may be substantially nonporous. Alternatively, the sheath 20 may be porous, for example, substantially continuously along its length or at one or more locations, e.g., to allow fluid delivered into the lumen 26 to pass through the wall of the sheath 20 in a desired manner, e.g., to deliver fluid to a wall of a vessel (not shown) through which the sheath 20 extends. In a further alternative, the sheath 20 may include one or more discrete openings (not shown) at one or more locations along its length.

In addition or alternatively, the sheath 20 may include a thin-walled metal foil. Alternatively, the sheath 20 may include a thin mesh, e.g. a perforated urethane film and the like. In a further alternative, the lubricity of the sheath 20 may be enhanced by providing a lubricious coating, lining, ribbing, and the like (not shown), and/or applying a lubricant, e.g., to the interior surface of the sheath 20. The sheath 20 may include a single layer or multiple layers of such materials, such that a desired flexibility and lubricity is achieved. Thus, the sheath 20 may easily expand and/or line a body lumen to reduce friction and/or accommodate instruments being advanced through the body lumen, as explained further below.

Optionally, the sheath 20 may include one or more reinforcing elements (not shown). For example, a wire, thread, filament, and the like, formed from plastic, glass, composite, and/or metal, may be attached to an outer surface, an inner surface, and/or embedded in a wall of the sheath 20. In addition or alternatively, the sheath 20 may include relatively thickened regions that may be formed directly from the wall material. The reinforcing element(s) may extend circumferentially and/or helically around the sheath 20, and/or may extend axially along the sheath 20, depending upon the reinforcement desired. The reinforcement element(s) may also bias the sheath 20 assume a desired shape or configuration when expanded towards the enlarged condition.

In alternative embodiments, the sheath may be a tubular structure or a partially tubular structure of braided material (not shown) that may be attached to a stiffening member to provide a sheath apparatus. For example, the sheath may be formed from one or more plastic and/or metal wires, threads, or other strands that are braided, woven, and/or knit into a tubular body or into a sheet whose edges may be attached to a stiffening member, similar to the embodiments described elsewhere herein. The braided strands may be compressed to the contracted condition by twisting, folding, crimping, and/or wrapping, as described above, and/or by axial translation, e.g., pulling opposite ends of the sheath away from one another to cause the braided strand(s) to compress radially under the axial tension.

The proximal end 22 of the sheath 20 may include an annular collar or handle that may facilitate manipulating the sheath 20 and/or inserting one or more instruments into the lumen 26. In addition or alternatively, the proximal end 22 may include a hemostatic valve (also not shown) that may substantially seal the lumen 26 from proximal flow of fluid, yet may allow instruments to be introduced into the lumen 26, as is known in the art. For example, as shown in FIGS. 1A and 1B, a toughy borst valve 23 may be provided on the proximal end 22 of the sheath 20, e.g., to control passage into the lumen 26. Alternatively, other structures may be provided, e.g., a slit valve adapter, a removable clamp, an o-ring, a side port, an adjustable fixation device, and the like (not shown), for selectively sealing the lumen 26, manipulating the sheath 20, and/or for facilitating introducing instruments into the sheath 20.

The distal end 24 of the sheath 20 may include a variety of configurations. For example, as shown in FIGS. 1A and 2A, the distal end 24 of the sheath 20 may be offset proximally from the distal tip 17 of the stiffening member 12. In addition, the distal end 24 may include a rounded shape (e.g., as shown in FIG. 2A), a beveled shape (e.g., as shown in FIG. 6), or other tapered shapes that may enhance atraumatic advancement of the apparatus 10.

Figure 6:
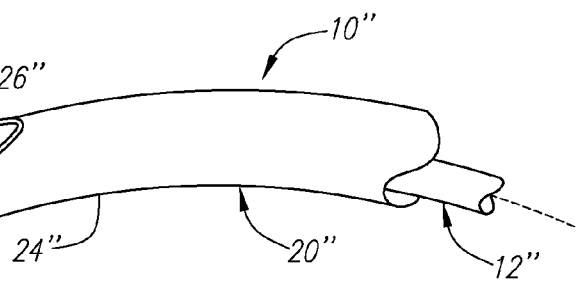
FIG. 6 is a perspective detail of an alternative distal end of a sheath apparatus, including an expandable sheath including a beveled distal end having an opening therein.

For example, as shown in FIG. 6, the taper 28" of the distal end 24" of the sheath 20" may facilitate tracking the apparatus 10" over a guide wire (not shown) and/or may facilitate advancing the apparatus 10" through a body lumen (also not shown). The taper 28" may minimize risk of the sheath 20" catching and/or may cause the sheath 20" to collapse towards the contracted condition as the apparatus 10" is advanced through a body lumen without needing external constraint. Alternatively, the distal end of the sheath may be substantially blunt (not shown).

The distal end 24 of the sheath 20 may be substantially closed or may include one or more openings. For example, as shown in FIG. 2A, the distal end 24 of the sheath 20 may be attached to the distal end 16 of the stiffening member 12 to substantially close the lumen 26 at the distal end 24. The distal end 24 of the sheath 20 may be detachable from the stiffening member 12 to release the sheath 20 from the stiffening member 12.

For example, the distal end 24 of the sheath 20 may be attached to the stiffening member 12 by an adhesive, solder, or other bonding materials, yet may be torn free or otherwise separated from the distal end 16 of the stiffening member 12, e.g., by pulling the sheath 20 proximally relative to the stiffening member 12 or by pushing the stiffening member 12 distally relative to the sheath 20. Alternatively, an instrument (not shown) may be advanced through the expandable member 20 and pushed against the closed distal end 24 to cause the distal end 24 to separate from the stiffening member 12. This may create an opening (not shown) in the distal end 24 of the sheath 20 through which fluid and/or one or more instruments (also not shown) may be advanced.

Alternatively, a mechanical connector (not shown) may be provided that may secure the distal ends 16, 24 together, and that may be actuated to release the distal end 24 of the sheath 20 from the distal end 16 of the stiffening member 12. In further alternatives, a cinch loop (not shown) may be provided on the distal end 24 that may be selectively opened or closed, or a removable clip (also not shown) may be provided. In addition or alternatively, the distal end 24 of the sheath 20 may be bonded to the distal end 16 of the stiffening member 12, e.g., using a bioabsorbable adhesive or other material that may dissolve when exposed to bodily fluids to provide an opening (not shown).

In a further alternative, shown in FIG. 5, the distal end 24' of the sheath 20' may include a break-away or penetrable region, e.g., a relatively thin or otherwise weakened region 30' of the sidewall of the sheath 20.' The weakened region 30' may tear along a weakened seam or may be punctured (not shown) when an instrument (also not shown) within the lumen 26' is pushed against the weakened region 30' to create an opening, thereby allowing the instrument to be advanced through the opening into the body lumen.

In yet another alternative, shown in FIG. 6, the distal end 24" of the sheath 20" may include one or more openings 28" communicating with the lumen 26," e.g., an axial opening defined by the tapered distal end 24," such that an instrument (not shown) inserted through the lumen 26" may be advanced from the opening 28" and into the body lumen.

Figure 7:
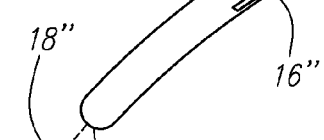
FIG. 7 is a side view of an alternative embodiment of a sheath apparatus, including an expandable sheath with an inflatable cuff on one end.

Alternatively, as shown in FIG. 7, the distal end 424 of the sheath 420 may include an expandable cuff 430. The cuff 430 may be an inflatable annular balloon attached around a periphery of the sheath 420. One or more lumens (not shown) may be provided within the stiffening member 412 that communicate with the interior of the cuff 430 to expand and/or collapse the cuff 430. The expanded cuff 430 may be used to fix the sheath 420 within a body lumen (not shown) and/or may serve to isolate a distal segment of a body lumen from a segment proximal to the expanded cuff 430.

For example, the sheath 420 may be delivered into a blood vessel, and the cuff 430 may be expanded to seal the vessel. One or more intravascular manipulations or procedures may be performed within the vessel proximal to the expanded cuff 430. Thus, if embolic debris is released within the proximal portion of the vessel, the cuff 430 may prevent the debris from passing to the distal portion of the blood vessel.

In another alternative, the proximal opening 426 of the sheath 420 may be positioned within a blood vessel (not shown), thereby creating a bypass or shunt channel that may be positioned within a body lumen beginning at the proximal opening 426 and extending through the lumen 426 of the sheath 420 to the distal cuff 430. In a further alternative, one or more lumens (not shown) may be created within or along a wall of the sheath 420 itself Optionally, one or more cuffs or pockets (not shown) may be provided at one or more locations along the sheath 420, e.g., to anchor the sheath 420, to restrict flow, e.g., for the purpose of retrograde infusion of contrast, and/or to bias the sheath 420 to expand to a particular shape or configuration.

Returning to FIGS. 1A-2B, in one embodiment, the sheath 20 may be a substantially enclosed tubular body that is attached to the stiffening member 12 at one or more locations between the proximal and distal ends of the stiffening member 12. For example, the sheath 20 may be attached to the stiffening member 12 only at the distal ends 24, 16. Alternatively, the sheath 20 may be attached to the stiffening member 12 at or near the proximal end 22, the distal end 24 of the sheath 20, or both, e.g., when the stiffening member 12 is disposed along a wall of the sheath 20.

Optionally, the sheath 20 may be attached to the stiffening member 12 intermittently, e.g., at one or more additional locations between the proximal and distal ends 22, 24. Alternatively, the stiffening member 12 may be attached substantially continuously to the sheath 20 between the proximal and distal ends 22, 24 of the sheath 20. The stiffening member 12 may be attached to an interior of the sheath 20, i.e., within the lumen 26, or, alternatively, may be attached to an exterior of the sheath 20. The sheath 20 and the stiffening member 12 may be attached to one another using any known method, e.g., bonding with adhesive, sonic welding, sutures or other strands (not shown) and the like.

Alternatively, as shown in FIGS. 21A and 21B, the stiffening member 12 may be received in a separate pocket or lumen 27 of the sheath 20 that extends between the proximal and distal ends 22, 24 of the sheath 20. The stiffening member 12 may be loose within the pocket or lumen 27 (FIG. 21) or may be attached to the sheath 20 within the lumen 27 (FIG. 21B), as described above.

In another embodiment, shown in FIGS. 4A and 4B, the sheath 120 may be a sheet of material whose edges 121 are attached to a stiffening member 112. Thus, the stiffening member 112 may partially define the lumen 126, along with the sheet of the sheath 120. The sheath 120 may be attached substantially continuously along the length of the stiffening member 112, although, alternatively, the sheath 120 may be attached intermittently to the stiffening member 112, as described previously.

Optionally, any of the sheaths described above, e.g., the sheath 20 shown in FIGS. 1A-2B may be configured to split, e.g., along one or more seams (not shown) extending at least partially from the proximal end 22 towards the distal end 24, and/or to separate from the stiffening member 12. For example, the sheath 20 may include two or more sets of intermittent perforations and/or relatively thin-walled seams (not shown) that extend between the proximal and distal ends 22, 24. In addition or alternatively, the material of the sheath 20 may be biased to tear preferentially, e.g., along the longitudinal axis 18, to separate the sheath 20 into two or more longitudinal strips (not shown). These features may facilitate removing the sheath 20 and/or the entire apparatus 10 from a body lumen when an instrument (not shown) is disposed within the lumen 26, for example, when the instrument is intended to be substantially permanently implanted within the body lumen.

Figure 8:
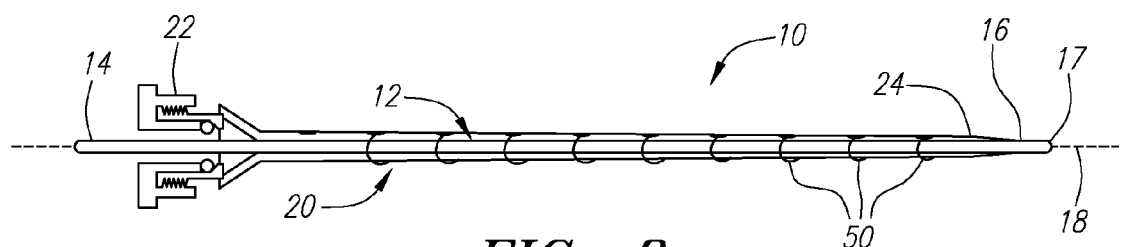
FIG. 8 is a partial cross-sectional side view of a sheath apparatus including wire loops wrapped around an expandable sheath to constrain the sheath in a contracted condition.

The apparatus 10 may also include a constraint for covering and/or protecting the sheath during advancement through a patient's vasculature or other body passages. For example, as shown in FIG. 8, one or more wires, threads, monofilaments, or other strands 50 may be disposed around the sheath 20 to maintain the sheath 20 in its contracted condition. The strands 50 may include a plurality of loops 52 that extend around the sheath 20 and are secured using one or more removable filaments (not shown) fed through the loops 52. To release the sheath 20, the removable filament(s) may be removed from the loops 52, e.g., by pulling the removable filament(s) from the proximal end of the apparatus 10. The loops 52 may then be released and their strand(s) may be removed.

Alternatively, other constraints, e.g., wraps, ties, adhesives, bio-absorbable encapsulating materials, e.g., sucrose, and the like, may be used (not shown). In further alternatives, a catheter, sheath, or other tubular member (also not shown) may be provided. For example, as shown in FIGS. 13A and 13B, a catheter 80 may be used that may include a lumen 82 within which the apparatus 10 (or any other sheath apparatus described herein) may be disposed when the sheath 20 is in the contracted condition. The apparatus 10 may include a pushing element 84, e.g., a wire or other elongate member extending from the stiffening member 12 (see FIGS. 1A-2B, not shown in FIGS. 13A and 13B). The pushing element 84 may be advanced distally relative to the catheter 80 to deploy the apparatus 10, as shown in FIG. 13B, or may be pulled proximally to retract the apparatus 10 into the catheter 80, as shown in FIG. 13A.

In another embodiment, shown in FIGS. 16A-17C, an outer sheath 180 maybe provided that is at least partially bonded to a sheath apparatus 110 to maintain an expandable sheath 120 in a contracted condition. The outer sheath 180 may be formed from materials similar to the expandable sheath 120, e.g., having a wall thickness between about 0.005-0.06 millimeter (mm). Thus, the outer sheath 180 may be substantially flexible and/or conformable to facilitate advancing the apparatus 110 and outer sheath 180 through a body lumen of a patient.

The apparatus 110 may include a stiffening member 112, similar to that described above with reference to FIGS. 3A-4B, to which the expandable sheath 120 may also be attached, similar to other embodiments described above. The stiffening member 112 may include one or more lumens 119 (three exemplary lumens being shown), and the outer sheath 180 may be bonded or otherwise attached to the stiffening member 112, e.g., continuously or intermittently along a length of the stiffening member 112. The lumen(s) in the stiffening member 112 may provide infusion, aspiration, agitation, and/or perfusion through the apparatus 110, e.g., from the proximal end to the distal end of the apparatus 110. Alternatively, the outer sheath 180 may be attached directly to the expandable sheath 120, e.g., at a location around the periphery and/or along a length of the expandable sheath 120 (not shown).

Figure 16A:
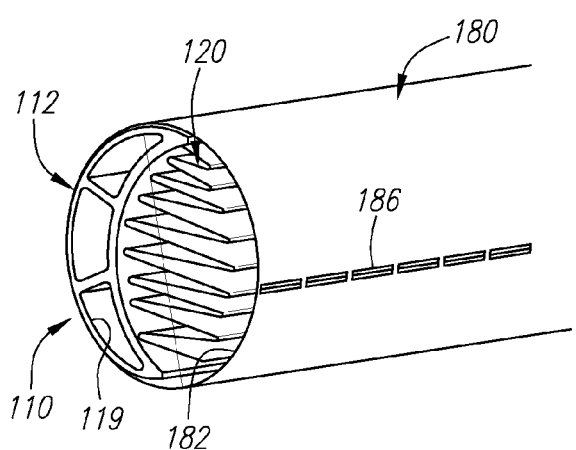
FIGS. 16A-16C are perspective details of another embodiment of a sheath apparatus including an outer sheath that may separate to accommodate expansion of an expandable sheath therein.
Figure 17A:
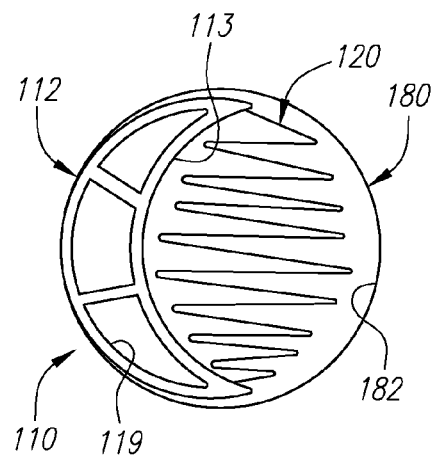
FIGS. 17A-17C are cross-sectional views of the apparatus shown in FIGS. 16A-16C, respectively.

As best seen in FIGS. 16A and 17A, the outer sheath 180 may at least partially define a lumen 182 (either alone or along with the stiffening member 112) within which the expandable sheath 120 may be received in its contracted condition. In addition, the outer sheath 180 may include one or more weakened regions 186, e.g., extending between proximal and distal ends (not shown) of the outer sheath 180. The weakened region(s) 186 may include intermittent perforations and/or continuous or intermittent thin-walled regions that may extend, e.g., substantially axially along the outer sheath 180.

The weakened region(s) 186 may separate upon exposure to internal pressure to allow the expandable sheath 120 to expand towards its enlarged condition. For example, fluid may be introduced into the lumen 182 of the outer sheath 180 until sufficient pressure develops to cause the weakened region(s) 186 to tear or otherwise separate. Alternatively, fluid or an instrument (not shown) may be introduced into the expandable sheath 120 such that the expandable sheath 120 expands until it pushes radially outwardly against the outer sheath 180 and causes the weakened region(s) 186 to separate.

Figure 16B:
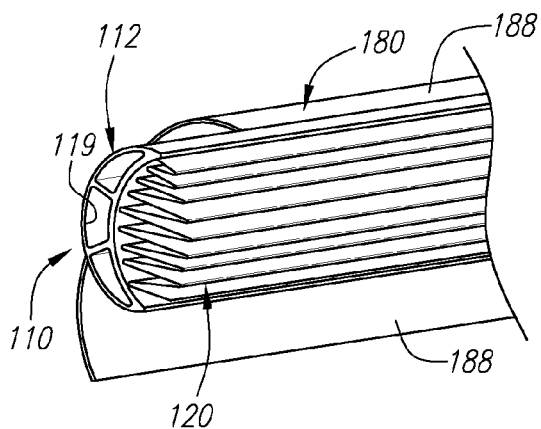
Figure 17B:
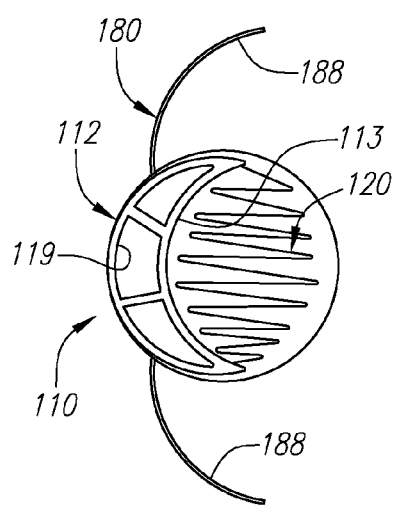
Figure 16C:
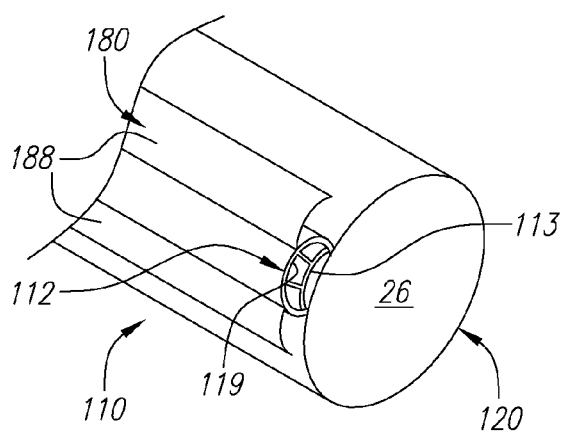
Figure 17C:
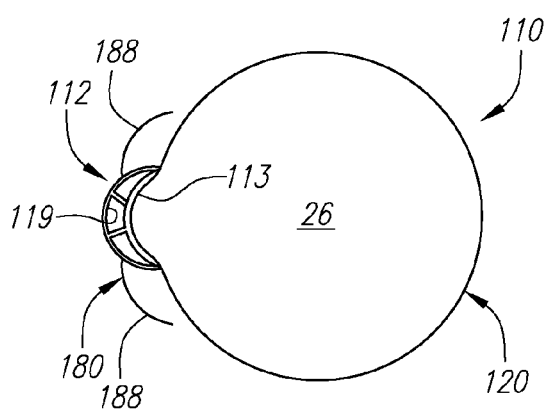

For example, during use, the apparatus 110 and outer sheath 180 may be advanced through a body lumen, e.g., a blood vessel and the like (not shown), with the outer sheath 180 intact and the expandable sheath 120 in its contracted condition, as shown in FIGS. 16A and 17A. Once a desired location is reached, internal pressure may be applied to separate the weakened region(s) 186 of the outer sheath 180, as shown in FIGS. 16B and 17B. The expandable sheath 120 may then be expanded to its enlarged condition, as shown in FIGS. 16C and 17C. The separated portions 188 of the outer sheath 180 may be substantially flexible such that they do not interfere substantially with the expansion of the expandable sheath 120 and/or may conform substantially to the shape of the expandable sheath 120 as it expands.

In a further alternative, with reference to FIGS. 1A-2B, when a constraint is provided around the sheath 20, the sheath 20 need not be attached to the stiffening member 12. The sheath 20, e.g., a tubular body, may simply be disposed around the stiffening member 12 and folded, twisted, crimped, wrapped, or otherwise compressed into the contracted condition around or adjacent to the stiffening member 12 before being inserted into or otherwise constrained by the constraint. In addition or alternatively, vacuum pressure, either alone or in conjunction with folding, may be used to compress the sheath 20 and/or fluid may be infused into the lumen 26 to expand the sheath 20, as explained further below.

Figure 9A:
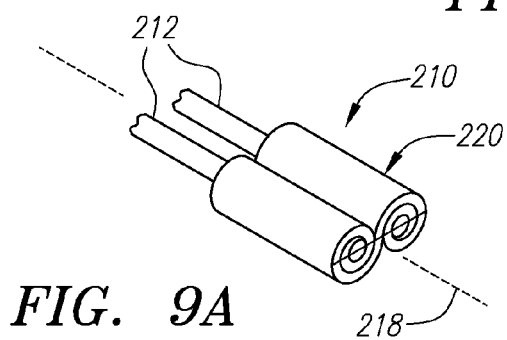
FIGS. 9A and 9B are perspective details of a sheath apparatus, showing an expandable sheath in contracted and expanded conditions, respectively.
Figure 9B:
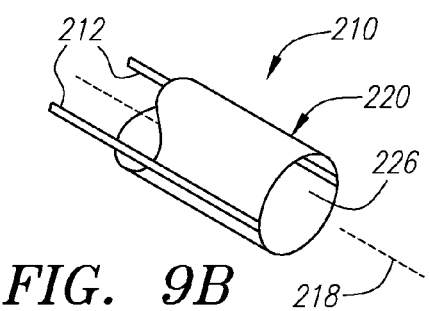

Although only one stiffening member 12 is shown in FIGS. 1A-2B, it will be appreciated that a sheath apparatus in accordance with the present invention may include more than one stiffening member. For example, as shown in FIGS. 9A and 9B, an embodiment of a sheath apparatus 210 is shown that includes two stiffening members 212 to which an expandable membrane or other sheath 220 is attached. The sheath 220 may be compressed to a contracted condition, shown in FIG. 9A, e.g., by twisting the stiffening members 212 about longitudinal axis 218 to wind the sheath 220 around the stiffening members 212. The sheath 220 may be unwound and expanded to an enlarged condition, shown in FIG. 9B, by untwisting the stiffening members 212, thereby providing lumen 226 within the sheath 220.

Figure 10A:
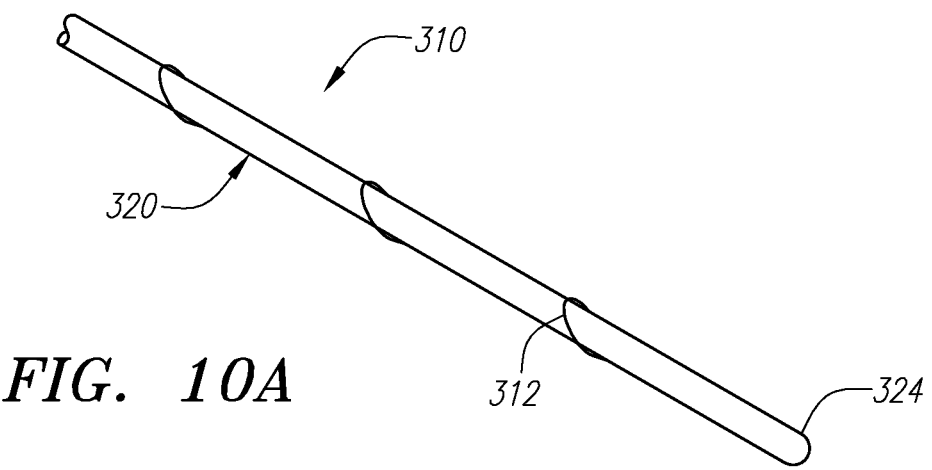
FIGS. 10A and 10B are perspective details of another embodiment of a sheath apparatus, showing an expandable sheath in contracted and expanded conditions, respectively.
Figure 10B:
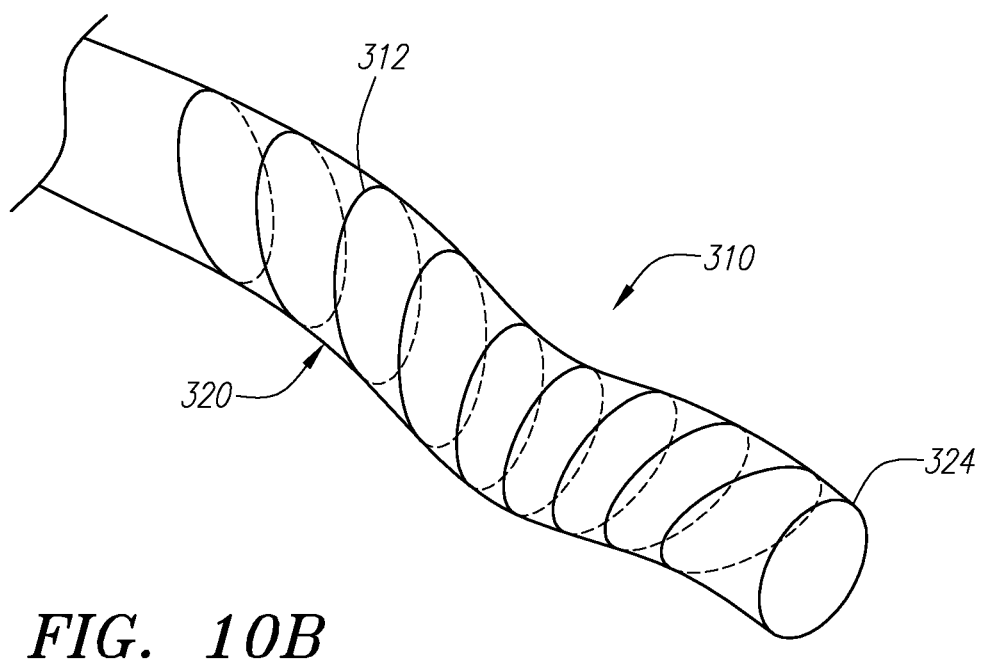

In addition, although the stiffening members 12, 212 shown in FIGS. 1A-2B, 9A, and 9B extend generally parallel to the longitudinal axis 18, 218, other stiffening members may also be provided in addition or instead of the stiffening member(s) 12, 212. For example, as shown in FIGS. 10A and 10B, one or more reinforcing members 312 may be provided that extend helically around a tubular sheath 320. The reinforcing members 312 may be wires or other strands attached to an outer or inner surface of the sheath 320 or embedded within a wall of the sheath 320. One or more helical reinforcing members may also facilitate expanding and/or collapsing the sheath 320. For example, ends of the reinforcing member(s) 312 may pulled axially away from one to compress the sheath 320. In addition or alternatively, the reinforcing member(s) 312 may be biased to expand, e.g., towards the configuration shown in FIG. 10B, to facilitate expanding the sheath 320 towards the enlarged condition.

In addition or alternatively, one or circumferential or peripheral rings or strands (not shown) may be provided around the sheath 320. Such reinforcing rings or strands may support the sheath 320 and/or bias the sheath 320 towards the enlarged condition, similar to the helical reinforcing member(s) described above.

Further, although the apparatus described above include an expandable sheath having a single lumen, it will be appreciated that it may be possible to provide one or more sheaths, each including one or more lumens therein. For example, a sheath may be fabricated to have multiple lumens, e.g. by extrusion. As a further example, a plurality of expandable sheaths, similar to those described above, may be attached to one another and/or to one or more common stiffening members to provide an apparatus with multiple expandable lumens (not shown). The sheaths may be concentric with one another, e.g., disposed loosely within one another, or attached along one or more edges to one another. Alternatively, the sheaths may be disposed adjacent to one another, e.g., attached together or to one or more common stiffening members. Thus, multiple instruments may be advanced through respective lumens of the sheaths in conjunction with one another.

Optionally, one or more of the components of the sheath apparatus described above, e.g., stiffening member(s), sheath, and/or constraint, may include one or more radiopaque markers, e.g., bands or other elements made from radiopaque material, radiopaque inks or other depositions, and the like (not shown). Such markers and/or radiopaque material may facilitate imaging and/or monitoring the apparatus during its use, e.g., using fluoroscopy. In addition, markers may be provided that are spaced relative to one another in a predetermined manner, e.g., at known distances from one another, to denote distances and/or facilitate mapping and/or accessing a patient's vasculature. Alternatively, other external or internal imaging systems and methods may be used, e.g., magnetic resonance imaging ("MRI"), ultrasound, and the like, as is well known in the art.

A sheath apparatus in accordance with the present invention may be used to provide access to a variety of body lumens, e.g., to perform a diagnostic and/or therapeutic procedure. Generally, the apparatus, with an expandable sheath in a contracted condition, may be introduced into an entry site, e.g., a natural or created opening in a patient's body, and advanced into one or more body passages, including created passages, e.g., dissection planes, within the patient's body. Preferably, the apparatus is advanced from the entry site until a distal end of the sheath is disposed within a target body lumen while a proximal end of the sheath remains outside the entry site. Because of its low profile, the apparatus may be easily advanced through tortuous anatomy until the distal end is disposed within relatively small, difficult to access body lumens.

The sheath may then be expanded to an enlarged condition, thereby defining a lumen within the sheath. Thus, the lumen defined by the sheath may extend from the entry site through any intervening body passages to the target body lumen or site to provide a path from the entry site to the target body lumen or site. Optionally, if, as described above, the sheath is maintained and/or covered in the contracted condition by a constraint, the constraint may be at least partially removed from the sheath before the sheath is expanded to the enlarged condition.

A diagnostic and/or therapeutic procedure, such as the exemplary procedures described below, may be performed within the body lumen via the lumen defined by the sheath. Upon completing the procedure(s), the sheath may be withdrawn from the body lumen, and preferably from the patient's body.

For example, as shown in FIGS. 11A-11F, a sheath apparatus 10 may be used to facilitate delivering a stent 60 within a stenosis or occlusion 92 within a blood vessel 90. The vessel 90 may be an artery or vein within a coronary, carotid, cerebral, or other vessel, e.g., within a patient's coronary, peripheral, or neuro vasculature.

Figure 11A:
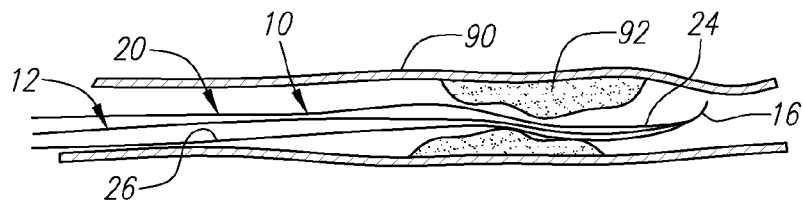
FIGS. 11A-11F are partial cross-sections of a patient's vasculature, showing a method for delivering a stent across a stenosis using a sheath apparatus, in accordance with the present invention.

As shown in FIG. 11A, the apparatus 10, with the sheath 20 in its contracted condition, may be advanced from a percutaneous entry site (not shown) and introduced into the patient's vasculature, until the distal end 16 is disposed within the target vessel 90. For example, a guidewire (not shown) may be previously placed from the percutaneous entry site to the vessel 90 beyond the stenosis 92 using conventional methods. The apparatus 10 may be advanced over the guidewire until the distal end 24 of the sheath 20 is positioned within or beyond the stenosis 92, as shown in FIG. 11A. If the apparatus 10 includes a stiffening member 12, the stiffening member 12 may include a guidewire lumen (not shown) such that the guidewire may be inserted through the guidewire lumen to advance the apparatus 10 over the guidewire. Alternatively, the sheath 20, in its contracted condition may be advanced without a previously placed guidewire. The distal tip of the sheath 20 or stiffening member 12 may facilitate navigation through the vasculature, e.g., by being substantially flexible or floppy, to avoid trauma to the vasculature during advancement, or by being shaped, shapeable, or deformable to enable steering during advancement.

Once the apparatus 10 is positioned within the vessel 90, any constraint (not shown) maintaining the sheath 20 in the contracted condition or otherwise covering the sheath 20 may be removed, e.g., mechanically, chemically (e.g., bioabsorbable sutures), and/or physiologically (e.g., heat-activated nitinol ties). For example, as described above, this may involve retracting an overlying catheter or sheath (not shown), or removing loops or other strands (also not shown) surrounding the sheath 20.

The sheath 20 may then be expanded from its contracted condition to its enlarged condition. For example, a fluid (not shown) may be introduced into the lumen 26 to expand the sheath 20, e.g., such that the sheath 20 expands to line or otherwise contact walls of one or more vessels within the patient's vasculature, e.g., between the entry site and the vessel 90. Alternatively, the sheath 20 may simply be released such that the sheath 20 is free to expand as one or more instruments, such as the catheter 62 and stent 60, are advanced through the lumen 26, as shown in FIG. 11B.

Figure 11B:
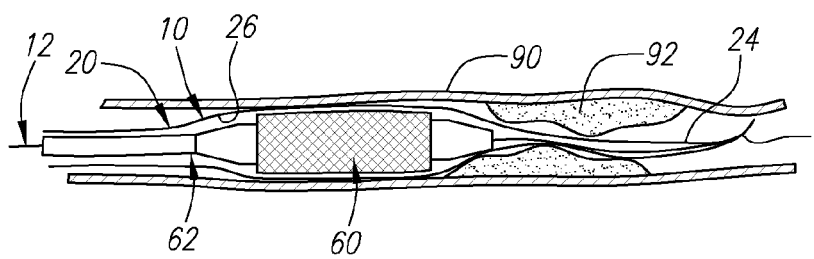

With continued reference to FIG. 11B, one or more instruments may be introduced through the lumen 26 defined by the sheath 20 into the vessel 90. For example, a catheter 62 carrying the stent 60 may be introduced into the proximal end 22 (not shown in FIGS. 1A-11F) of the sheath 20 and advanced through the lumen 26 until the stent 60 is located within the vessel 90. The stent 60 may be any known endoprosthesis, e.g., a balloon-expandable or self-expanding stent, and the catheter 62 may include any known delivery apparatus, e.g., including a balloon, sheath, nose cone, and/or other elements. Optionally, other instruments, e.g., thrombectomy devices, agitation devices, balloon catheters, filters, occlusion devices, and the like (not shown) may be introduced through the sheath 20 before or after the catheter 62, e.g., to dilate the stenosis 92 and/or to provide distal protection, i.e., capture embolic material released during the procedure.

The guidewire or other rail over which the apparatus 10 may be advanced may be removed before any instrument(s) are advanced through the sheath 20, or the guidewire may remain in place across the stenosis 92. In addition, if the apparatus 10 includes a concentric stiffening member 12 within the sheath 20, the catheter 62 may be advanced over the stiffening member 12, i.e., between the stiffening member 12 and the sheath 20 as shown in FIG. 11B. Alternatively, the stiffening member 12 may be removed from the sheath 20 if the sheath is detachable from the stiffening member 12 (not shown). In a further alternative, such as that shown in FIGS. 4A and 4B, the instrument(s) (not shown in FIGS. 4A and 4B) may be advanced through the lumen 126 adjacent to the stiffening member 12. Thus, one advantage of delivering a catheter or other instrument within the sheath 20 is that there may be no need for a guidewire lumen in the instrument, which may allow the profile of the instrument to be reduced as compared to instruments that are delivered over a guidewire.

Figure 11C:
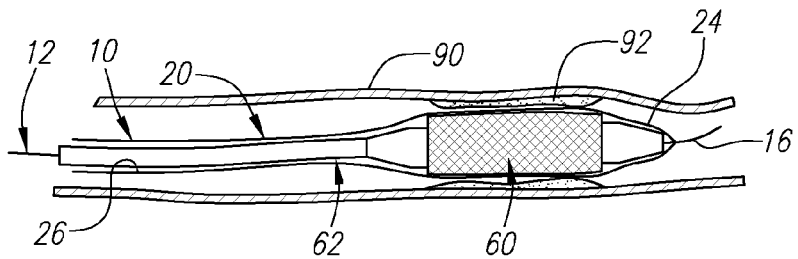

With continued reference to FIG. 11B, the lubricious nature of the sheath 20 may facilitate advancing the catheter 62 through the lumen 26, and, consequently, through any narrow, tortuous, diseased, and/or friable regions of the patient's vasculature. For example, the sheath 20 may translate axial forces, e.g., created when an instrument, such as the catheter 62, is pushed against or into a narrow region, into radial forces that may facilitate dilating the narrow region to accommodate the instrument passing therethrough. This action may be enhanced further by pressurizing the sheath 20 internally, e.g., by introducing a fluid into the lumen 26. Thus, the sheath 20 may facilitate advancing the stent 60 across the stenosis 92, as shown in FIG. 11C.

In addition, the sheath 20 may substantially reduce the risk of perforating or otherwise damaging the walls of vessels within the vasculature and/or snagging an instrument, since the sheath 20 may guide any instruments advanced through the sheath 20 along the lubricious path of the lumen 26. Further, the sheath 20 may minimize the risk of embolic material and the like from being dislodged from the patient's vasculature, since the sheath 20 may expand to line the walls, thereby restraining plaque, thrombus, and the like between the sheath 20 and the vessels' walls.

Figure 11D:
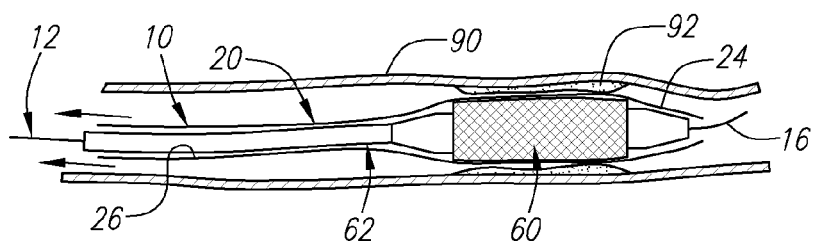

If the distal end 24 of the sheath 20 is closed, an opening 28 may be created to accommodate advancing one or more instruments through the lumen 26 and out of the sheath 20. For example, as explained above, the distal end 24 may be separated from the stiffening member 12 when the first instrument, e.g., the catheter 62 carrying the stent 60 is advanced through the lumen 26 and against the distal end 24, as shown in FIG. 11D. Alternatively, if the distal end 24 of the sheath 20 is attached to a stiffening member 12, the distal end 24 may be separated from the stiffening member 12, e.g., by advancing the stiffening member 12 distally and/or retracting the sheath 20 proximally, to create the opening 28, e.g., before or after introducing the catheter 62 or other instrument (not shown) into the lumen 26.

In a further alternative, as shown in FIG. 5 and described above, the sheath 20' may include a weakened region 30' in the distal end 24' that may be used to create an opening (not shown in FIG. 5). For example, a fluid, e.g., saline and/or contrast, may be introduced into the lumen 26' of the sheath 20' until sufficient internal pressure is created to cause the weakened region 30' to rupture or tear. Alternatively, an instrument (e.g., the catheter 62 shown in FIGS. 11B-11F, a guidewire, and the like, not shown), may be advanced into the lumen 26' and pushed against the weakened region 30' to cause the weakened region 30' to fail and create an opening. In still a further alternative, an apparatus 10," such as that shown in FIG. 6, may be used that includes a sheath 20" with an opening 28" already provided in the distal end 24."

Figure 11E:
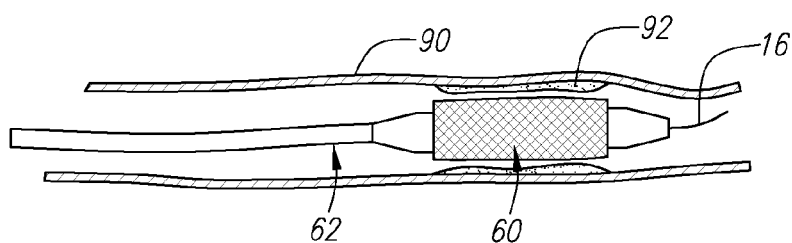
Figure 11F:
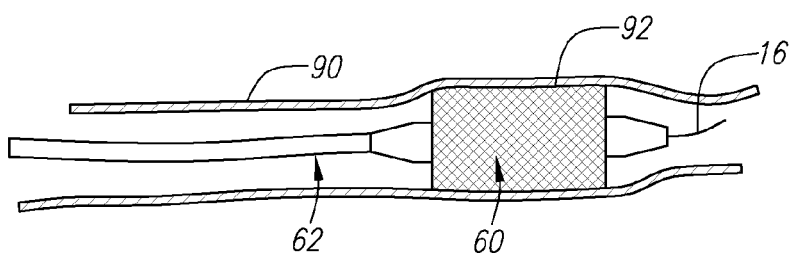

Turning to FIG. 11E, once the stent 60 is positioned across the stenosis 92, the sheath 20 may be at least partially retracted to expose the stent 60 and/or the catheter 62 within the vessel 90 and/or stenosis 92. The stent 60 may be expanded, as shown in FIG. 11F, e.g., using conventional methods to dilate and/or scaffold the stenosis 92. Once the stent 60 is delivered (and any additional procedures completed), the catheter 62 and the apparatus 10 may be removed from the vessel 90, and the patient's vasculature via the entry site.

In one embodiment, the catheter 62 or other instruments (not shown) may first be removed into and through the sheath 20, whereupon the sheath 20 may be removed. If desired, the sheath 20 may be collapsed at least partially from the enlarged condition before removing the sheath 20 from the vessel 90 by aspirating any fluid from within the lumen 26 of the sheath 20, e.g., by connecting a source of vacuum to the proximal end 22 of the sheath 20. Alternatively, a catheter or other tubular member (not shown) may be advanced over the sheath 20 to facilitate its removal. In another alternative, the sheath 20 may be removed simultaneously with the catheter 62 or other instrument(s), e.g., by retracting the instrument(s) into the sheath 20. In yet another alternative, the sheath 20 may be removed from the patient before the catheter 62 or other instrument(s) are removed. It will be appreciated that external imaging, e.g., fluoroscopy, MRI, and/or ultrasound, may be used to monitor the procedure, and that any of the components, e.g., the apparatus 10, the stent 60, and/or the catheter 62 may include elements, e.g., radiopaque markers (not shown) for facilitating such imaging during their advancement and/or removal.

Turning to FIGS. 12A-12D, another method is shown that uses a sheath apparatus 10 (or any of the sheath apparatus described above) for providing access to a target vessel within a patient's vasculature. Specifically, the apparatus 10 may be used to deliver an electrical lead 70, e.g., for a pacemaker, into a coronary vein 96, e.g., adjacent to the left ventricle of the heart. As shown in FIG. 12A, initially, the apparatus 10 may be advanced into the coronary vein 96 with an expandable sheath 20 carried by a stiffening member (not shown) in its contracted condition.

For example, with the sheath 20 collapsed, the apparatus 10 may be introduced from a percutaneous entry site (not shown), e.g., a femoral vein or subclavian vein, and advanced through the patient's venous system into the right atrium of the heart, and into the coronary sinus (not shown) to reach the target coronary vein 96. The apparatus 10 may be advanced over a guidewire (not shown), similar to the previous methods. Because of its relatively low profile, the apparatus 10 may be able to access smaller coronary veins or be advanced further into a target coronary vein than conventional devices.

Once the apparatus 10 is positioned within or near a target vein 96, fluoroscopy and/or other external imaging may be used to facilitate positioning the apparatus 10. The apparatus 10, e.g., the distal end 24 of the sheath 20, an overlying constraint, and the like (not shown), may include one or more radiopaque markers (not shown) to facilitate such imaging. In addition or alternatively, contrast may be introduced into the vein, e.g., via a fluid lumen in a stiffening member (not shown) of the apparatus 10 and/or through the lumen 26 of the sheath 20, to facilitate fluoroscopic imaging. Such imaging may be used to identify the location of the sheath 20 relative to nearby structures, e.g., to ensure that the apparatus 10 is advanced as close as possible to a target location. Preferably, the apparatus 10 is advanced such that the distal end 24 of the sheath 20 is disposed within a coronary vein 96 adjacent the left ventricle of the patient's heart (not shown).

As shown in FIG. 12B, the sheath 20 may be expanded between the entry site and the target vein 96. If a constraint (not shown) is provided, it may be removed before expanding the sheath 20. A fluid, e.g., including saline and/or contrast, may be introduced into the sheath 20 to expand the sheath 20 towards its enlarged condition. Contrast delivered into the sheath 20 may also facilitate imaging the vein 96. For example, if the distal end 24 of the sheath 20 is initially closed, contrast delivered into the lumen 26 may cause the sheath 20 to expand and conform to the shape of the surrounding vessels, thereby facilitating imaging of the vessels through which the sheath 20 is deployed.

As shown in FIGS. 12B and 12C, an electrical pacing lead 70 may be advanced through the lumen 26 of the sheath 20 until a tip 72 of the lead 70 is disposed within the target vein 96. Similar to the methods described above, the sheath 20 may already include an opening 28 in its distal end 24 that communicates with the lumen 26 or an opening may be created in a closed sheath distal end 24 (not shown). The tip 72 may be deployed from the sheath 20, e.g., by retracting the sheath 20 or advancing the tip 72 through the opening 28 beyond the distal end 24 of the sheath 20, thereby substantially anchoring the tip 72 within the vein 96.

As shown in FIG. 12D, the sheath 20 may then be removed from the vein 96 and from the patient's vasculature. Preferably, the sheath 20 may be split into one, two, or more pieces to allow the sheath 20 to be removed easily from around the lead 70. Implantation of the lead 70 may then be completed using conventional methods.

Turning to FIGS. 14A-14C, another method is shown for delivering a colonoscope 76 into a patient's colon 98 using a sheath apparatus 10, such as any of the embodiments described above. As shown in FIG. 14A, the apparatus 10 is advanced into the colon 98 with the sheath 20 in its contracted condition. Once advanced to a desired location, the sheath 20 may be expanded to an enlarged condition to define a lumen 26, as shown in FIG. 14B. The colonoscope 76 may be advanced through the lumen 26 of the sheath 20, similar to the previous embodiments. If desired, the sheath 20 may be configured such that the colonoscope 76 may image surrounding tissue within the colon 76 as the colonoscope 76 is advanced through the sheath 20. For example, the material of the sheath 20 may be substantially transparent to visible light (or other portions of the spectrum) that is used by the colonoscope 76. Alternatively, in other applications, the sheath 20 may allow other imaging sources, e.g., ultrasound energy, to pass substantially freely through the sheath 20 to allow imaging of the surrounding tissue. The sheath 20 may be removed from around the colonoscope 76, as shown in FIG. 14C, or may remain at least partially around the colonoscope 76, e.g., to facilitate its removal after a procedure. In addition, the sheath 20 may be adapted for introducing fluid, e.g., air, carbon dioxide and the like, into the gastrointestinal lumen.

Figure 15A:
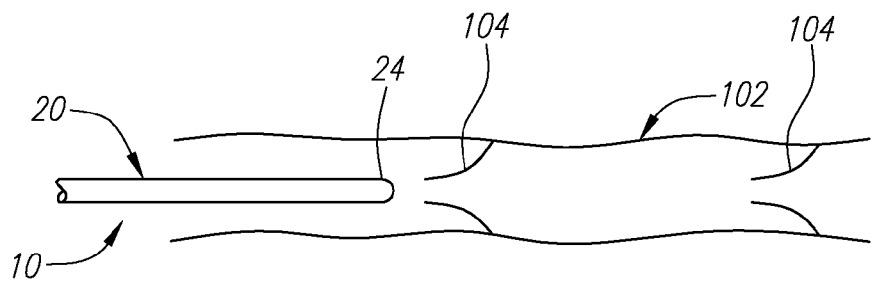
FIGS. 15A-15D are partial cross-sectional views of a vein, showing a method for delivering a stent through valves of the vein.
Figure 15B:
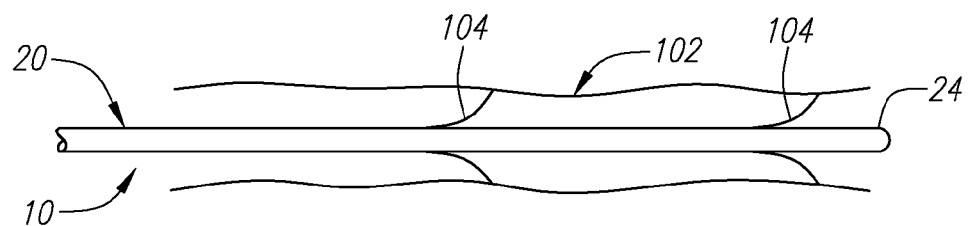
Figure 15C:
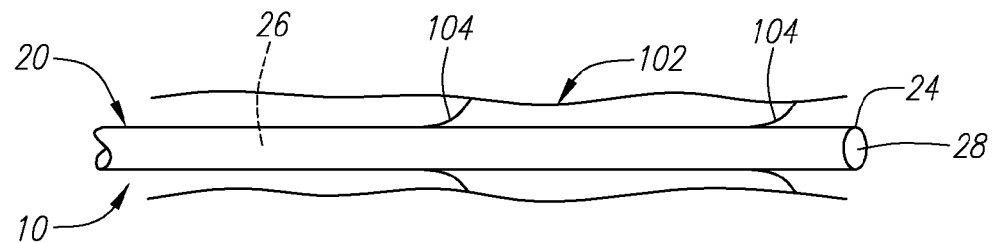
Figure 15D:
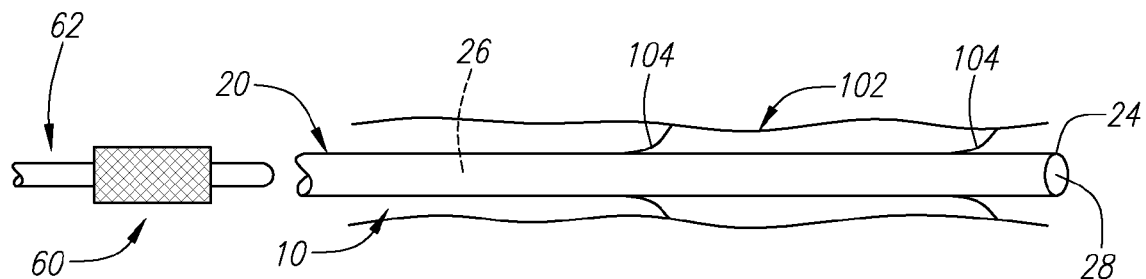

Turning to FIGS. 15A-15D, a sheath apparatus in accordance with the present invention may facilitate advancement of one or more instruments retrograde into a patient's venous system. For example, as shown in FIG. 15A, an exemplary vein 102 is shown that includes a plurality of valves 104. A sheath apparatus 10 (which may be any of the embodiments described herein) may be advanced into the vein 102 with an expandable sheath 20 in its contracted condition, as shown in FIG. 15B. Once advanced to a desired position, the sheath 20 may be expanded to its enlarged condition, as shown in FIG. 15C, thereby opening the valves 104 and provided a relatively large bore lumen 26 through the vein 102. One or more instruments, such as the stent 60 and catheter 60 shown in FIG. 14D, may be advanced through the lumen 26 to complete a procedure, similar to the embodiments described above.

A sheath apparatus according to the present invention may also be used to perform other diagnostic and/or therapeutic procedures within the vasculature. For example, the apparatus may provide an expandable lumen for delivering an imaging element, e.g., an intravascular ultrasound ("IVUS") device, endoscope, fiber optic element, and the like, and/or for delivering therapeutic instruments, e.g., angioplasty catheters, stent delivery devices, atherectomy or thrombectomy devices, and the like.

In alternative methods, a sheath apparatus in accordance with the present invention may be used to provide access and/or deliver instruments to other body lumens within a patient's body. For example, the apparatus may be used within a patient's urogenital tract, respiratory tract, gastrointestinal tract, lymphatic system, or vascular system. In addition, the apparatus may be introduced into surgically created openings and advanced into surgically created passageways, e.g., a passageway created within interstitial space, e.g. to obtain a biopsy.

Turning to FIGS. 18 and 19A-19C, another embodiment of a sheath apparatus 510 is shown, in accordance with the present invention. Generally, the apparatus 510 includes a catheter or other elongate member 512 and an expandable sheath 520. The catheter 512 may be an elongate tubular body formed from uniform or variable flexibility material, e.g., having a substantially flexible distal end 514. The catheter 512 may include one or more lumens (not shown) extending from its proximal end (also not shown) to the distal end 514.

In a preferred embodiment, the catheter 512 includes one or more diagnostic or therapeutic elements 516 on the distal end 514. For example, the catheter 512 may include an imaging element, such as an intravascular ultrasound ("IVUS") device, and the like, and/or a dissection element, such as a cutting element, an element for blunt dissection, or an ablation element, e.g., for observing, crossing, and/or treating an occlusion within a blood vessel (not shown). In addition or alternatively, the catheter 512 may include a steering element (also not shown) for manipulating the distal end 514 within a patient's body.

The sheath 520 may be a substantially flexible, and preferably flimsy, membrane or other structure. For example, the sheath 520 may include any of the materials and/or structures included in any of the embodiments described previously. The sheath 520 may be substantially permanently attached to an outer surface 518 of the catheter 512. For example, the sheath 520 may include a sheet whose longitudinal edges are attached at one or more locations along a length of the catheter 512. Alternatively, the sheath 520 may be a tubular member having an outer surface that is attached at one or more locations along the length of the catheter 512. Thus, the sheath 520 may extend at least partially between the proximal end and the distal end 514 of the catheter 512.

Figure 19A:
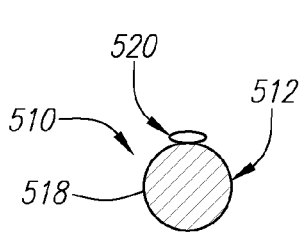
FIGS. 19A-19C are cross-sections of the apparatus of FIG. 18, showing the sheath contracted, expanded, and with a guidewire therein, respectively.
Figure 19B:
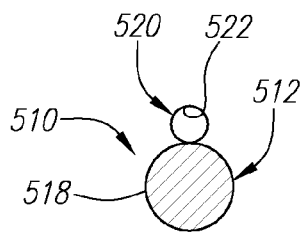
Figure 19C:
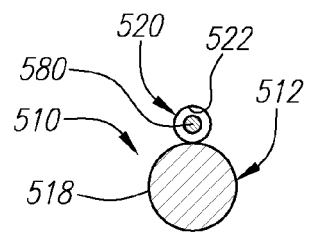

The sheath 520 may be expandable from a contracted condition (shown in FIG. 19A), e.g., to minimize a profile of the sheath 520, and an enlarged condition (shown in FIGS. 19B and 19C). In the enlarged condition, the sheath 520 may at least partially define an accessory lumen 522. The accessory lumen 522 may extend between a proximal end (not shown) and a distal end 524 of the sheath 520, preferably terminating adjacent the distal end 514 of the catheter 512.

The distal end 524 of the sheath 520 may include an opening (not shown) communicating with the accessory lumen 522. Alternatively, the distal end 524 may be closed, and may include a break-away portion for creating an opening (not shown) such that an instrument (such as a guidewire 580, shown in FIG. 19C) inserted through the lumen 522 may be advanced from the opening into a body lumen, similar to the previous embodiments.

Optionally, a constraint (not shown) may be provided for maintaining the sheath 520 in the contracted condition, e.g., as the apparatus 510 is advanced through a patient's body. For example, an outer sheath (not shown) may be provided for receiving the catheter 512 and the sheath 520) that may be removed before the sheath 520 is expanded. In addition or alternatively, an adhesive may be used to temporarily secure the sheath 520 along the outer surface 518 of the catheter 512. Thus, the adhesive may retain the sheath 520 substantially flat along the outer surface 518 of the catheter 512, as shown in FIG. 19A. The adhesive may release when internal pressure is delivered into the lumen 522 of the sheath 520 or may dissolve within a body lumen to release the sheath 520 to allow the sheath 520 to expand.

Figure 18:
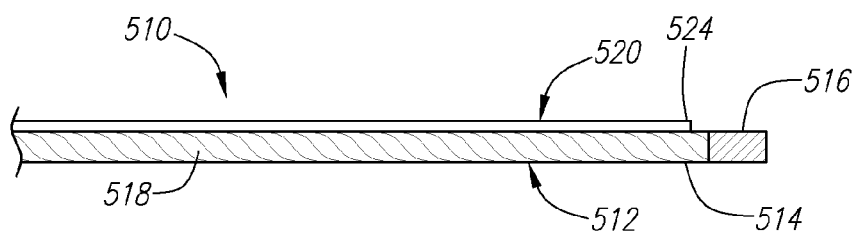
FIG. 18 is a side view of another embodiment of an apparatus including a catheter and an expandable sheath, in accordance with the present invention.
Figure 20A:
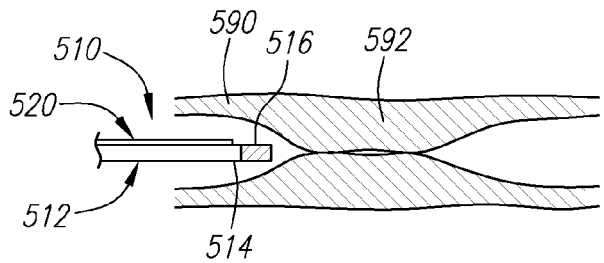
FIGS. 20A-20D are cross-sectional views of a blood vessel, showing a method for delivering a guidewire across an occlusion in the vessel.

Turning to FIGS. 20A-20D, a method is shown for delivering an instrument, e.g., a guidewire 580 through a total occlusion 592, e.g., within a blood vessel or other body lumen 590, e.g., using the apparatus 510 shown in FIG. 18. Initially, as shown in FIG. 20A, with the sheath 520 in its contracted condition, the apparatus 510 may be introduced into the vessel 590, e.g., via a percutaneous entry site (not shown), until the distal end 514 of the catheter 512 is located proximally (e.g., upstream) relative to the occlusion 592.

Figure 20B:
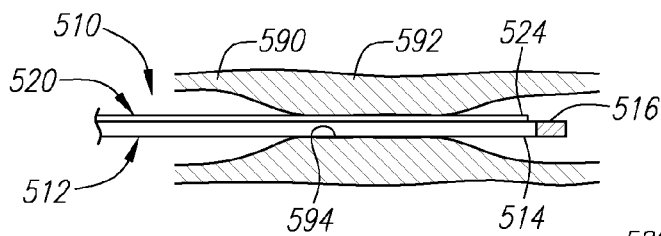
Figure 20C:
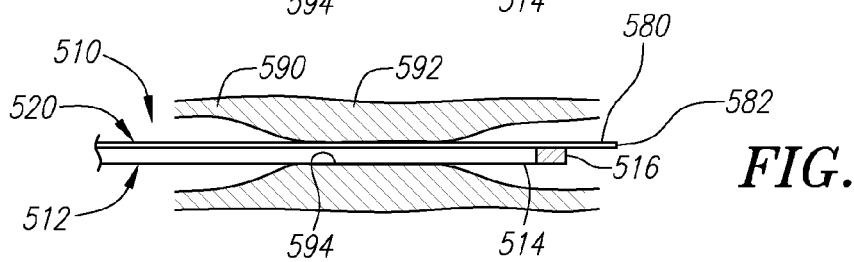
Figure 20D:
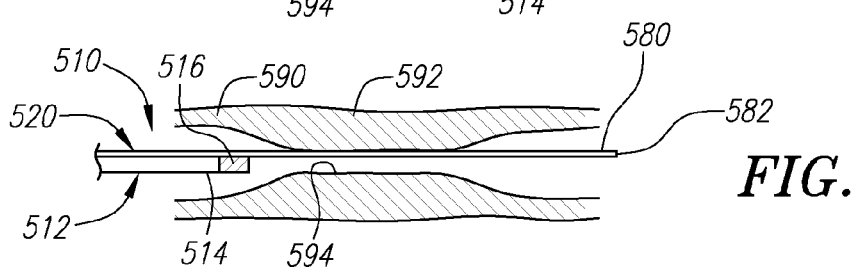

Turning to FIG. 20B, the distal end 514 of the catheter 512 maybe advanced through the occlusion 592 until the distal end 524 of the sheath 520 is disposed distally (e.g., downstream) relative to the occlusion 592. The catheter 512 may include one or more elements 516 on the distal end 514 for facilitating advancing the catheter 512 through the occlusion 592. For example, the catheter 512 may carry an imaging element, e.g., an IVUS device (not shown), on the distal end 514 for imaging the occlusion. In addition or alternatively, a dissection element, e.g., a cutting, core, blunt dissection, and/or ablation element (not shown), may be provided on the distal end 514 for creating a passage 594 through the occlusion. Optionally, the catheter 512 may include a steering element (not shown) to facilitate manipulating the distal end 514 of the catheter 512 as it is advanced through the occlusion 592.

Once the sheath 520 extends through the occlusion 592, an elongate member, e.g., a guidewire 580 or other instrument (not shown), may be inserted through the sheath 520 until a distal end 582 of the guidewire 580 is disposed distal to the occlusion 592. The sheath 520 may be expanded as the guidewire 580 or other instrument is advanced through the sheath 520. Alternatively, the sheath 520 may be dilated, e.g., by introducing a fluid into the lumen 522 (see FIG. 29B) of the sheath 520, similar to the embodiments described above.

The apparatus 510 may then be withdrawn through the occlusion 592 and/or out of the vessel 590. One or more instruments (not shown) may then be advanced over the guidewire 592, e.g., to treat the occlusion 592 and/or to deliver agents or fluids distally beyond the occlusion 592, as is well known to those skilled in the art. Thus, unlike the previous embodiments, the sheath 520 may provide a lumen for a secondary device, e.g., a guidewire, that may be delivered in cooperation with the catheter 512.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for providing access to a body lumen of a patient, comprising:
    a flexible stiffening member having a proximal end and a distal end having a size and shape for insertion into a body lumen and defining a maximum outer cross-section, the stiffening member being flexible to facilitate advancement through tortuous anatomy; and
    an expandable sheath extending from the proximal end to the distal end of the stiffening member and attached to the stiffening member distal end, the sheath being expandable from a contracted condition to minimize a profile of the sheath to allow insertion along with the stiffening member into a body lumen, and an enlarged condition wherein the sheath at least partially defines a lumen extending between the proximal and distal ends of the stiffening member, the lumen having an inner diameter larger than the maximum outer cross-section of the distal end of the stiffening member.

2. The apparatus of claim 1, wherein the stiffening member comprises a distal tip that extends beyond the distal end of the sheath.

3. The apparatus of claim 1, wherein the stiffening member comprises a substantially atraumatic distal tip.

4. The apparatus of claim 1, wherein the stiffening member is received in a separate pocket or lumen of the sheath that extends between proximal and distal ends of the sheath.

5. The apparatus of claim 4, wherein the stiffening member is attached to the sheath within the lumen.

6. The apparatus of claim 1, wherein the sheath comprises a lubricious material.

7. The apparatus of claim 1, wherein the stiffening member comprises an elongate member extending substantially parallel to a longitudinal axis of the sheath.

8. The apparatus of claim 1, wherein the sheath is attached to the stiffening member at one or more locations.

9. The apparatus of claim 8, wherein the sheath is attached to the stiffening member at the proximal and distal ends of the stiffening member.

10. The apparatus of claim 8, wherein the sheath is attached substantially continuously to the stiffening member between the proximal and distal ends of the stiffening member.

11. The apparatus of claim 1, wherein the stiffening member comprises a guidewire lumen extending between the proximal and distal ends, the guidewire lumen having an inner diameter smaller than the inner diameter of the lumen of the expandable sheath in the enlarged condition.

12. The apparatus of claim 1, further comprising a "J" tip on the distal end of the stiffening member.

13. The apparatus of claim 1, wherein the stiffening member has a maximum outer cross-section between about 0.05-5 millimeters.

14. The apparatus of claim 1, wherein the stiffening member has a maximum outer cross-section between about 0.2-2 millimeters.

15. The apparatus of claim 1, further comprising a handle on the proximal end of the sheath and wherein the sheath extends from the handle to the stiffening member distal end.

16. An apparatus for providing access to a body lumen of a patient, comprising:
a flexible stiffening member having a proximal end, a distal end having a size and shape for insertion into a body lumen and defining a maximum outer cross-section, the stiffening member being flexible to facilitate advancement through tortuous anatomy and having sufficient length to be advanced from a location outside a patient's body through any intervening body passages into a site to be accessed; and
an expandable sheath expandable from a contracted condition to minimize a profile of the sheath and an enlarged condition, the expandable sheath being flimsy and extending between the proximal and distal ends of the stiffening member, the sheath being expandable from the contracted condition to allow insertion along with the stiffening member into a body lumen, and the enlarged condition wherein the sheath at least partially defines a lumen extending between the proximal and distal ends of the stiffening member, the lumen of the sheath having an inner diameter larger than the maximum outer cross-section of the distal end of the stiffening member in the enlarged condition.

17. The apparatus of claim 16, wherein the sheath may be split into one or more pieces to allow the sheath to be removed easily from around an electrical lead advanced through the lumen of the sheath.

18. The apparatus of claim 16, further comprising an electrical lead that may be advanced through the lumen of the sheath after the sheath has been advanced along with the stiffening member to the site to be accessed.

19. The apparatus of claim 16, wherein the stiffening member is received in a separate pocket or lumen of the sheath that extends between proximal and distal ends of the sheath.

20. The apparatus of claim 16, wherein the stiffening member extends substantially parallel to a longitudinal axis of the sheath.

21. The apparatus of claim 16, wherein the sheath is attached to the stiffening member at one or more locations.

22. The apparatus of claim 16, the stiffening member further comprising one or more lumens extending between the proximal and distal ends.

23. The apparatus of claim 16, wherein the apparatus has a low profile defining an outer diameter or other maximum cross-section when the expandable sheath is in the contracted condition, and wherein the inner diameter of the lumen is between about three and ten times larger than the diameter or other maximum cross-section of the low profile of the apparatus.

24. The apparatus of claim 16, wherein the apparatus defines an outer diameter or other maximum cross-section between about 0.1 and about ten millimeters (0.1-10 mm) when the expandable sheath is in the contracted condition, and wherein the inner diameter of the lumen of the expandable sheath is larger than the outer diameter or other maximum cross-section of the apparatus when expanded to the enlarged condition.

25. An apparatus for providing access to a body lumen of a patient, comprising:
a flexible stiffening member having a proximal end, a distal end having a size and shape for insertion into a body lumen, and one or more lumens extending between the proximal and distal ends; and
an expandable sheath extending from the proximal end to the distal end of the stiffening member, the sheath being expandable from a contracted condition to minimize a profile of the sheath to allow insertion along with the stiffening member into a body lumen, and an enlarged condition wherein the sheath at least partially defines a lumen extending between the proximal and distal ends of the stiffening member, the sheath comprising a lubricious coating for facilitating inserting one or more instruments through the lumen,
wherein the apparatus has an outer profile when the expandable sheath is in the contracted condition between about 0.1 and about ten millimeters (0.1-10 mm), and wherein the expandable sheath defines a lumen in the enlarged condition that is larger than the outer profile and having a diameter or other maximum cross-section between about 0.3 and about one hundred millimeters (0.3-100 mm).

26. A system for treating a patient via a body lumen, comprising:
a flexible stiffening member having a proximal end, and a distal end having a size and shape for insertion into a body lumen and defining an outer diameter;
an expandable sheath extending between the proximal and distal ends of the stiffening member, the sheath being expandable from a contracted condition to minimize a profile of the sheath to allow insertion along with the stiffening member into a body lumen, and an enlarged condition wherein the sheath at least partially defines a lumen extending between the proximal and distal ends of the stiffening member, the lumen of the sheath having an inner diameter in the enlarged condition larger than the outer diameter of the distal end of the stiffening member; and
an electrical lead advanceable through the lumen of the sheath after the sheath has been advanced along with the stiffening member into a desired body lumen of a patient,
wherein the sheath comprises a lubricious coating for facilitating inserting the lead through the lumen.

27. An apparatus for providing access to a body lumen of a patient, comprising:
an expandable flimsy, inelastic sheath comprising a proximal end, a distal end, and a length sufficient for the sheath to extend between an entry site into a patient's body and a target body lumen, the sheath being expandable from a contracted condition to minimize a profile of the sheath to allow insertion into a body lumen, and an enlarged condition wherein the sheath at least partially defines a lumen extending between the proximal and distal ends; and one or more flexible reinforcing members extending along the sheath, the one or more reinforcing members having a cross-section smaller than the lumen of the sheath in the enlarged condition, wherein the apparatus has an outer profile when the expandable sheath is in the contracted condition defining a first diameter or other maximum cross-section, and wherein the expandable sheath defines a lumen having a second inner diameter or other maximum cross-section in the enlarged condition that is between about three and ten times larger than the first diameter or other maximum cross-section of the outer profile of the apparatus.

* * * * *